United States Patent
Nordquist et al.

(10) Patent No.: US 12,336,870 B2
(45) Date of Patent: Jun. 24, 2025

(54) THREADED CONNECTOR PORT CLEANING SYSTEM, METHOD, AND APPARATUS

(71) Applicant: Avent, Inc., Alpharetta, GA (US)

(72) Inventors: Jeffrey S. Nordquist, Lake Barrington, IL (US); Crystal Koelper, North Barrington, IL (US); Shawn Purnell, Canton, GA (US); Robert McVey, Arlington Heights, IL (US)

(73) Assignee: Avent, Inc., Alpharetta, GA (US)

( * ) Notice: Subject to any disclaimer, the term of this patent is extended or adjusted under 35 U.S.C. 154(b) by 748 days.

(21) Appl. No.: 17/546,127

(22) Filed: Dec. 9, 2021

(65) Prior Publication Data

US 2022/0096814 A1    Mar. 31, 2022

Related U.S. Application Data

(62) Division of application No. 15/147,139, filed on May 5, 2016, now Pat. No. 11,224,732.

(Continued)

(51) Int. Cl.
*A61B 90/70* (2016.01)
*A47L 13/46* (2006.01)
(Continued)

(52) U.S. Cl.
CPC .............. *A61B 90/70* (2016.02); *A47L 13/46* (2013.01); *A61J 15/0026* (2013.01);
(Continued)

(58) Field of Classification Search
CPC .......... A47L 13/16; A47L 13/44; A47L 13/46; A61B 90/70; A61B 2090/701; A61J 15/0026; A46B 2200/3013; B08B 9/021
(Continued)

(56) References Cited

U.S. PATENT DOCUMENTS 3,061,861 A * 11/1962 Hartmann ............... A47L 13/25
                                                        15/244.1
3,290,711 A * 12/1966 Swanson ................. B08B 9/021
                                                         15/67

(Continued)

FOREIGN PATENT DOCUMENTS

EP    0 441 171 A2    8/1992
JP    2001-309973 A    11/2001
(Continued)

OTHER PUBLICATIONS

Lumaclean, LLC, EnClean Brush, copyright 2015, 3 pages, internet link: http://encleantube.com/index.html.
(Continued)

*Primary Examiner* — Laura C Guidotti
(74) *Attorney, Agent, or Firm* — Meunier Carlin & Curfman LLC

(57) ABSTRACT

Systems, methods, and apparatus for cleaning and sealing threaded connector ports are disclosed. An exemplary cleaning system includes a basin and cleaning apparatus including a sealing connector, an alignment peg, and an outer foam sleeve having a tubular portion. The sealing connector includes a body portion having a gripping portion, an internal thread cleaning portion, and a longitudinal axis. Another cleaning apparatus also includes a cap cleaning end having a cap cavity and an inner foam pad. Another system includes a threaded connector port and a cleaning apparatus including an alignment peg, a disposable foam platform, and a handle body, which includes a grip portion and a pair of cleaning arms. The cleaning arms and foam pads are adapted to engage the female threads of a threaded connector port. A sealing apparatus includes a disposable liner having locator flaps and a placement tool having a handle and locator fingers.

14 Claims, 30 Drawing Sheets

Related U.S. Application Data

(60) Provisional application No. 62/157,223, filed on May 5, 2015.

(51) Int. Cl.
*A61J 15/00* (2006.01)
*B08B 9/02* (2006.01)
*A61M 39/16* (2006.01)
*A61M 39/20* (2006.01)

(52) U.S. Cl.
CPC ...... *B08B 9/021* (2013.01); *A46B 2200/3013* (2013.01); *A61M 39/162* (2013.01); *A61M 39/20* (2013.01)

(58) Field of Classification Search
USPC ........................................ 15/104.011, 104.05
See application file for complete search history.

(56) References Cited

U.S. PATENT DOCUMENTS

| | | | |
|---|---|---|---|
| 4,836,214 A | 6/1989 | Sramek | |
| 4,921,481 A | 5/1990 | Danis et al. | |
| 5,807,345 A | 9/1998 | Grabenkort | |
| 6,334,064 B1 | 12/2001 | Fiddian-Green | |
| 6,357,447 B1 | 3/2002 | Swanson et al. | |
| 7,818,155 B2 | 10/2010 | Stuebe et al. | |
| 8,147,486 B2 | 4/2012 | Honour et al. | |
| 8,252,247 B2 | 8/2012 | Ferlic | |
| 8,613,702 B2 | 12/2013 | Feer et al. | |
| 8,777,504 B2 | 7/2014 | Shaw et al. | |
| 8,986,230 B2 | 3/2015 | Nishtala | |
| 9,179,971 B2 | 11/2015 | Kirschenman | |
| 9,226,878 B2 | 1/2016 | Elia et al. | |
| 9,295,395 B2 | 3/2016 | Elia et al. | |
| 9,532,739 B2 | 1/2017 | Bennett-Guerrero | |
| 9,610,227 B2 | 4/2017 | Elia | |
| 9,642,779 B2 | 5/2017 | Elia et al. | |
| 9,713,579 B2 | 7/2017 | Elia et al. | |
| 10,220,419 B2 | 3/2019 | Ryan et al. | |
| 10,391,294 B2 | 8/2019 | Drmanovic | |
| 2008/0097179 A1 | 4/2008 | Russo | |
| 2008/0167607 A1 | 7/2008 | Pfeiffer et al. | |
| 2008/0249467 A1 | 10/2008 | Burnett et al. | |
| 2009/0008393 A1 | 1/2009 | Howlett et al. | |
| 2009/0062766 A1 | 3/2009 | Howlett et al. | |
| 2010/0003067 A1 | 1/2010 | Shaw et al. | |
| 2010/0064456 A1 | 3/2010 | Ferlic | |
| 2011/0030726 A1 | 2/2011 | Vaillancourt et al. | |
| 2011/0054440 A1 | 3/2011 | Lewis | |
| 2011/0265825 A1 | 11/2011 | Rogers et al. | |
| 2012/0016256 A1 | 1/2012 | Mabary et al. | |
| 2012/0039764 A1 | 2/2012 | Solomon et al. | |
| 2012/0216359 A1* | 8/2012 | Rogers | B08B 1/00 15/104.93 |
| 2012/0277619 A1 | 11/2012 | Starkebaum et al. | |
| 2013/0197485 A1 | 8/2013 | Gardner et al. | |
| 2013/0225946 A1 | 8/2013 | Feer et al. | |
| 2016/0074648 A1 | 3/2016 | Kerr et al. | |
| 2016/0113843 A1 | 4/2016 | Elia et al. | |
| 2016/0129223 A1 | 5/2016 | Kirschenman | |
| 2016/0214142 A1 | 7/2016 | Davis et al. | |
| 2016/0331298 A1 | 11/2016 | Burnett et al. | |
| 2017/0071502 A1 | 3/2017 | Bennett-Guerrero | |
| 2017/0202750 A1 | 7/2017 | Elia | |
| 2018/0078195 A1 | 3/2018 | Sutaria et al. | |
| 2018/0161249 A1 | 6/2018 | Elia et al. | |
| 2018/0289536 A1 | 10/2018 | Burnett | |

FOREIGN PATENT DOCUMENTS

| | | |
|---|---|---|
| JP | 2006-075356 A | 3/2006 |
| JP | 2010516342 A | 5/2010 |
| JP | 2011-526810 A | 10/2011 |
| JP | 2013503702 A | 2/2013 |
| WO | WO 92/17150 | 10/1992 |
| WO | WO 2006/019782 A2 | 2/2006 |
| WO | WO 2008/089196 A2 | 7/2008 |
| WO | WO 2014/077906 A1 | 5/2014 |
| WO | WO 2015/044904 A1 | 4/2015 |

OTHER PUBLICATIONS

Neomed, Inc., The NeoMed Loyalty Program, copyright 2016, 4 pages, internet link: http://www.neomedinc.com/wp oontent/uploads/2016/04/N M-SMM-100-Rev-O .pdf.
International Search Report issued in corresponding international application No. PCT/US2016/030942, mailed Jul. 6, 2016 (6 pages).
Written Opinion issued in corresponding international application No. PCT/US2016/030942, mailed Jul. 6, 2016 (4 pages).

\* cited by examiner

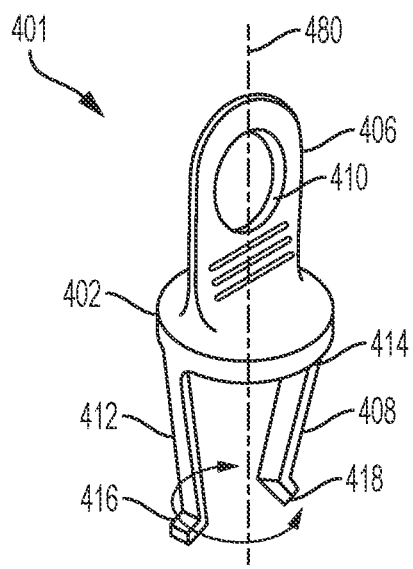
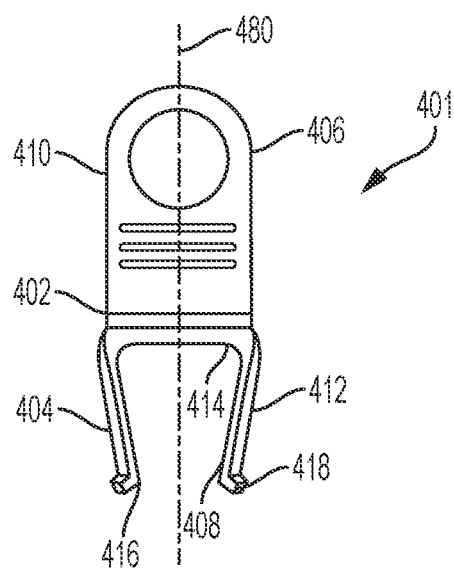
FIG. 4A  FIG. 4B
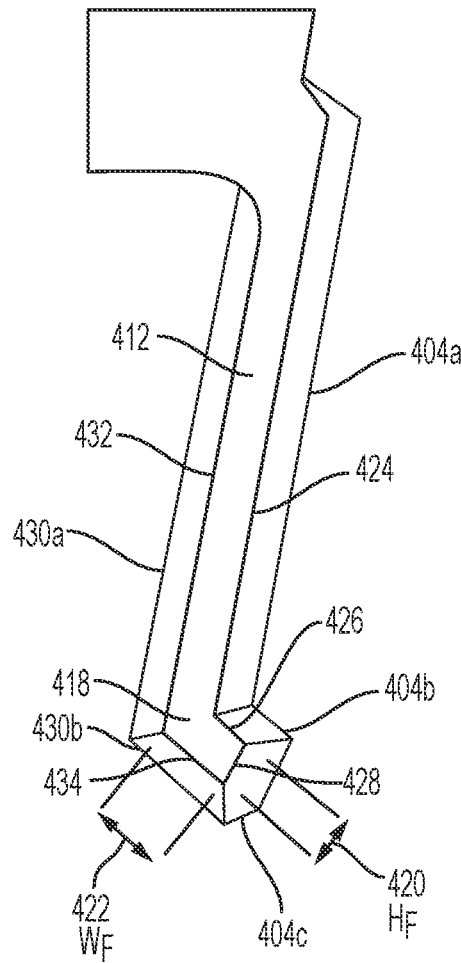
FIG. 4C

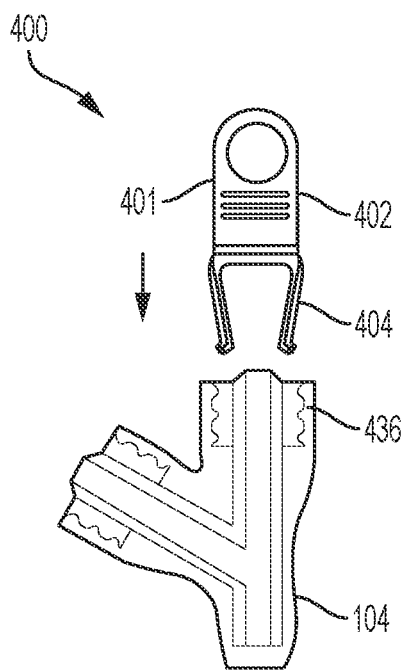 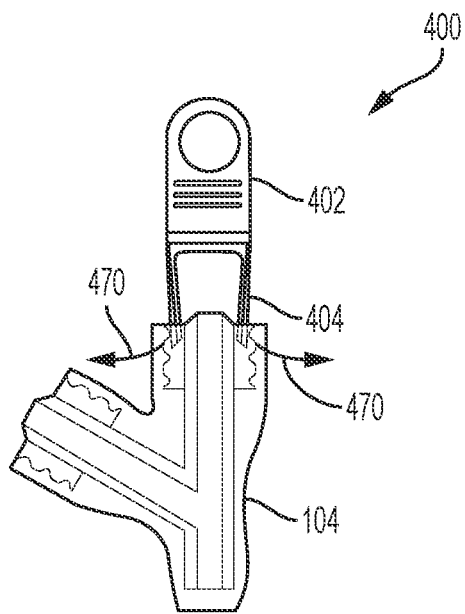
FIG. 4D  FIG. 4E
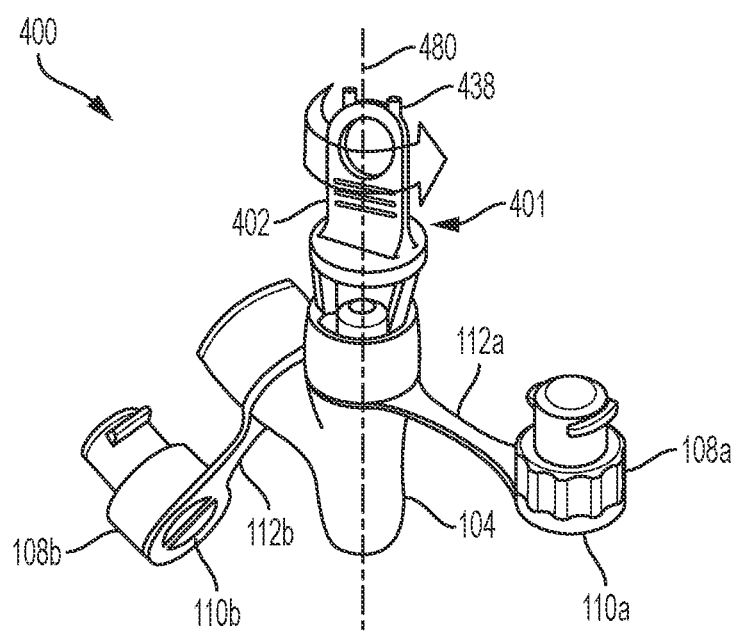
FIG. 4F

THREADED CONNECTOR PORT CLEANING SYSTEM, METHOD, AND APPARATUS

PRIORITY CLAIM AND CROSS-REFERENCE TO RELATED APPLICATIONS

The present application is a divisional of U.S. patent application Ser. No. 15/147 139, filed May 5, 2016, which claims priority to and the benefit of U.S. Provisional Patent Application Ser. No. 62/157,223, filed May 5, 2015, the entire contents of each of which are hereby incorporated by reference herein.

TECHNICAL FIELD

The present disclosure relates in general to a system, method, and apparatus for cleaning a threaded connector port used in medical tubing systems and/or medical small bore tubing systems, and more specifically for components used in systems for feeding, gastric decompression, residual volume measurement, and/or medicating patients using tubular delivery.

BACKGROUND

The use of connector ports is commonly required in various medical systems that utilize multiple components to deliver or remove one or more fluids to a patient or other person or animal being treated. One example of such a system is an enteral feeding system in which fluid nutrient formula or the like is delivered via a series of tubing segments to a patient. In such systems, it may be desirable to use one or more connectors to introduce a second fluid (e.g., a medication, flushing solution, or additional nutrient formula) into the fluid delivery apparatus. Such connectors can also be utilized in the opposite flow direction, for example, to collect stomach aspirate, reflux, or gasses escaping from the patient's gastrointestinal tract. Typically, threaded connector ports may require cleaning on a periodic basis. The current systems and methods employed in the prior art for cleaning a threaded connector port used in a medical tubing system for feeding, gastric decompression, residual volume measurement, and/or medicating patients may be improved upon as presently disclosed.

SUMMARY

The present disclosure provides a new and innovative system, method, and apparatus for cleaning threaded connector ports in medical tubing systems. In an exemplary aspect of the present disclosure, a cleaning apparatus for use in connection with a threaded connector port for a feeding tube includes a sealing connector, an alignment peg, and an outer foam sleeve. The sealing connector includes a body portion having a first end and a second end, an internal thread cleaning portion, and a longitudinal axis. The body portion includes a gripping portion. The internal thread cleaning portion is provided at the second end of the body portion. Additionally, the internal thread cleaning portion includes a location tube having a first length. The longitudinal axis extends from the first end of the body portion of the sealing connector to the internal thread cleaning portion of the sealing connector. The location tube is aligned with the longitudinal axis of the sealing connector. Additionally, the alignment peg is aligned with the longitudinal axis of the sealing connector and coupled to the second end of the body portion. The alignment peg has an outside diameter smaller than an internal diameter of a bore channel of the threaded connector port. The outer foam sleeve has a tubular portion having an interior surface, an exterior surface, and a second length. The interior surface of the tubular portion is coupled to the location tube. The tubular portion is adapted to engage a plurality of female threads of the threaded connector port along the second length of the tubular portion. Additionally, the exterior surface of the tubular portion has a predetermined diameter such that, upon inserting the alignment peg into the bore channel of the threaded connector port and rotating the body portion radially about the longitudinal axis of the sealing connector, the outer foam sleeve is forced outwardly into close contact with the plurality of female threads of the threaded connector port.

In accordance with another exemplary aspect of the present disclosure, which may be used in combination with the preceding aspect, a cleaning system for use in connection with a threaded connector port for a feeding tube includes a cleaning apparatus and a basin. The cleaning apparatus includes a sealing connector, an alignment peg, and an outer foam sleeve. The sealing connector includes a body portion having a first end and a second end, an internal thread cleaning portion, and a longitudinal axis. The body portion includes a gripping portion. The internal thread cleaning portion is provided at the second end of the body portion. Additionally, the internal thread cleaning portion includes a location tube having a first length. The longitudinal axis extends from the first end of the body portion of the sealing connector to the internal thread cleaning portion of the sealing connector. The location tube is aligned with the longitudinal axis of the sealing connector. Additionally, the alignment peg is aligned with the longitudinal axis of the sealing connector and coupled to the second end of the body portion. The alignment peg has an outside diameter smaller than an internal diameter of a bore channel of the threaded connector port. The outer foam sleeve has a tubular portion having an interior surface, an exterior surface, and a second length. The interior surface of the tubular portion is coupled to the location tube. The tubular portion is adapted to engage a plurality of female threads of the threaded connector port along the second length of the tubular portion. Additionally, the exterior surface of the tubular portion has a predetermined diameter such that, upon inserting the alignment peg into the bore channel of the threaded connector port and rotating the body portion radially about the longitudinal axis of the sealing connector, the outer foam sleeve is forced outwardly into close contact with the plurality of female threads of the threaded connector port. The basin has a side wall and a base forming a cavity with an opening. The cavity has a cavity depth and a cavity diameter and is at least partially filled with a wetting fluid. The cavity depth is greater than or equal to the length of the alignment peg, and the cavity diameter is greater than an external diameter of the outer foam sleeve. Additionally, the sealing connector is adapted to seal the opening of the basin.

In accordance with another exemplary aspect of the present disclosure, which may be used in combination with any one or more of the preceding aspects, a cleaning apparatus for use in connection with a threaded connector port for a feeding tube includes a handle body, an alignment peg, and a disposable foam platform. The handle body has a longitudinal axis extending from a first end of the handle body to a second end of the handle body, the handle body includes a pair of gripping arms extending upwards from the first end of the handle body and a pair of cleaning arms extending downwards from the second end of the handle body, the pair of cleaning arms are pivotally connected to the gripping arms by a pivot pin enclosed within the handle body, and the pair of cleaning arms are urged apart by applying a pressure at the pair of gripping arms in an inward direction towards the longitudinal axis of the handle body such that the pressure is transferred through the pivot pin to urge the pair of cleaning arms apart. The alignment peg is aligned with the longitudinal axis of the handle body and coupled to the second end of the handle body, the alignment peg has an outside diameter smaller than an internal diameter of a bore channel of the threaded connector port and has a length extending beyond the pair of cleaning arms. The disposable foam platform is coupled to the second end of the handle body, the disposable foam platform includes a tubular hollow portion aligned with the longitudinal axis of the handle body, the disposable foam platform has an attachment end and a cleaning end, the attachment end of the disposable foam platform is coupled to the second end of the handle body, the attachment end of the disposable foam platform includes a pair of cavities for receiving the pair of cleaning arms, and the cleaning end of the disposable foam platform is adapted to clean a plurality of female threads of the threaded connector port and the exterior surface of the bore channel within the threaded connector port when the alignment peg is inserted into the bore channel of the threaded connector port and the handle body is rotated radially about the longitudinal axis relative to the threaded connector port.

In accordance with another exemplary aspect of the present disclosure, which may be used in combination with the preceding aspect, the handle body includes at least two pairs of cleaning arms.

In accordance with another exemplary aspect of the present disclosure, which may be used in combination with any one or more of the preceding aspects, the disposable foam platform includes at least two pairs of cavities for receiving the cleaning arms.

In accordance with another exemplary aspect of the present disclosure, which may be used in combination with any one or more of the preceding aspects, the handle body includes at least two scallops adapted to assist in the removal of the disposable foam platform.

In accordance with another exemplary aspect of the present disclosure, which may be used in combination with any one or more of the preceding aspects, a cleaning system for use in connection with enteral feeding includes a threaded connector port and a cleaning apparatus for use in connection with the threaded connector port for a feeding tube. The cleaning apparatus includes a handle body, an alignment peg, and disposable foam platform. The handle body has a longitudinal axis extending from a first end to a second end of the handle body. The handle body includes a pair of gripping arms that are pivotally connected to a pair of cleaning arms by a pivot pin enclosed within the handle body. The cleaning arms are urged apart or together by applying pressure on the gripping arms in an inward or outward direction. The alignment peg is coupled to the handle body and has an outside diameter smaller than an internal diameter of a bore channel of the threaded connector port. The alignment peg has a length extending beyond the pair of cleanings arms. The disposable foam platform is coupled to the handle body and includes a tubular hollow portion, an attachment end, and a cleaning end. The attachment end of the disposable foam platform includes a pair of cavities for receiving the pair of cleaning arms, and the cleaning end is adapted to clean the female threads of the threaded connector port and the exterior surface of the bore channel.

In accordance with another exemplary aspect of the present disclosure, which may be used in combination with any one or more of the preceding aspects, a cleaning system for use in connection with enteral feeding includes a foam platform dispenser housing and a cleaning apparatus including a handle body and an alignment peg. The handle body has a longitudinal axis extending from a first end to a second end of the handle body, a pair of gripping arms extending upwards from the first end, and a pair of cleaning arms extending downwards from the second end of the handle body, the pair of cleaning arms are pivotally connected to the pair of gripping arms by a pivot pin enclosed within the handle body. The alignment peg is aligned with the longitudinal axis of the handle body and coupled to the second end of the handle body, the alignment peg has an outside diameter smaller than an internal diameter of a bore channel of the threaded connector port and has a length extending beyond the pair of cleaning arms. The alignment peg is adapted to be inserted into the bore channel of the threaded connector port such that the disposable foam platform cleans the female threads of the threaded connector port and the exterior surface of the bore channel within the threaded connector port when the handle body is rotated radially about the longitudinal axis relative to the threaded connector port. While rotating the handle body, the clinician may apply pressure to the gripping arms to urge the cleaning arms together or apart to assist in cleaning the female threads of the threaded connector port and the exterior surface of the bore channel.

The foam platform dispenser housing includes a front side and back side, the front side has a plurality of attachment end openings and the back side has a plurality of cleaning end openings, the plurality of attachment end openings are axially aligned with the plurality of cleaning end openings and the openings are adapted for receiving disposable foam platforms to be dispensed. Each disposable foam platform includes a tubular hollow portion, an attachment end, and a cleaning end. The attachment end includes a pair of cavities. The cleaning end is adapted to clean the female threads of a threaded connector port and the exterior surface of a bore channel within the threaded connector port. The cleaning apparatus and the foam platform dispenser are adapted to cooperate in dispensing the disposable foam platform, from the foam platform dispenser to the cleaning apparatus, in response to the handle body being axially aligned with one of the attachment end openings, the second end of the handle body being pressed onto the attachment end of the disposable foam platform to engage the pair of cavities with the pair of cleaning arms of the handle body, and the attachment end of the disposable foam platform being coupled to the second end of the handle body.

In accordance with another exemplary aspect of the present disclosure, which may be used in combination with any one or more of the preceding aspects, a cleaning system for use in connection with enteral feeding includes a threaded connector port, a foam platform dispenser housing, and a cleaning apparatus. The cleaning apparatus includes a handle body and an alignment peg. The handle body has a longitudinal axis extending from a first end to a second end of the handle body, a pair of gripping arms extending upwards from the first end, and a pair of cleaning arms extending downwards from the second end of the handle body, the pair of cleaning arms are pivotally connected to the pair of gripping arms by a pivot pin enclosed within the handle body. The alignment peg is aligned with the longitudinal axis of the handle body and coupled to the second end of the handle body, the alignment peg has an outside diameter smaller than an internal diameter of a bore channel of the threaded connector port and has a length extending beyond the pair of cleaning arms. The alignment peg is adapted to be inserted into the bore channel of the threaded connector port such that the disposable foam platform cleans the female threads of the threaded connector port and the exterior surface of the bore channel within the threaded connector port when the handle body is rotated radially about the longitudinal axis relative to the threaded connector port. The foam platform dispenser housing includes a front side and back side, the front side has a plurality of attachment end openings and the back side has a plurality of cleaning end openings, the plurality of attachment end openings are axially aligned with the plurality of cleaning end openings and the openings are adapted for receiving disposable foam platforms to be dispensed. Each disposable foam platform includes a tubular hollow portion, an attachment end, and a cleaning end. The attachment end includes a pair of cavities, and the cleaning end is adapted to clean the female threads of a threaded connector port and the exterior surface of a bore channel within the threaded connector port. The cleaning apparatus and the foam platform dispenser are adapted to cooperate in dispensing the disposable foam platform, from the foam platform dispenser to the cleaning apparatus, in response to the handle body being axially aligned with one of the attachment end openings, the second end of the handle body being pressed onto the attachment end of the disposable foam platform to engage the pair of cavities with the pair of cleaning arms of the handle body, and the attachment end of the disposable foam platform being coupled to the second end of the handle body.

In accordance with another exemplary aspect of the present disclosure, which may be used in combination with any one or more of the preceding aspects, a cleaning apparatus includes a handle body and a first plurality of foam pads. The handle body includes a longitudinal axis extending from a first end of the handle body to a second end of the handle body, the first end includes a grip portion and the second end includes at least two cleaning arms, the cleaning arms each have a proximal end and a terminal end distally located from the handle body, each of the terminal ends of the cleaning arms have an outward facing flange having a height and width adapted to engage a female thread of the threaded connector port, the cleaning arms include a first outer surface, a second outer surface, and a third outer surface along the length of the cleaning arm and outward facing flange, the first outer surface extends from the proximal end of the cleaning arms to the terminal end of the cleaning arms, the second outer surface extends from the terminal end of the cleaning arms along the width of the outward facing flange, and the third outer surface extends from the second outer surface along the height of the outward facing flange. Each foam pad of the plurality of foam pads is respectively coupled to the first outer surface, the second outer surface, and the third outer surface on each of the cleaning arms, and the foam pads are adapted to clean the female threads of the threaded connector port as the flanges maintain outward pressure on the foam pads while the handle body is inserted into the threaded connector port and rotated radially about the longitudinal axis of the handle body.

In accordance with another exemplary aspect of the present disclosure, which may be used in combination with any one or more of the preceding aspects, the handle body includes a pair of cleats adapted to engage a top surface of a threaded connector port cap when unscrewing the threaded connector port cap.

In accordance with another exemplary aspect of the present disclosure, which may be used in combination with any one or more of the preceding aspects, the cleaning arms have different lengths.

In accordance with another exemplary aspect of the present disclosure, which may be used in combination with any one or more of the preceding aspects, the cleaning apparatus further comprises a second plurality of foam pads, each foam pad of the second plurality of foam pads is respectively coupled to a first inner surface and a second inner surface, the first inner surface extends from the proximal end of the cleaning arms to the terminal end of the cleaning arms, and the second inner surface extends from the terminal end of the cleaning arms along the width of the outward facing flange.

In accordance with another exemplary aspect of the present disclosure, which may be used in combination with any one or more of the preceding aspects, the cleaning apparatus includes a sealing connector, a location tube, an inner foam pad, and an outer foam sleeve. The sealing connector includes a body portion having a gripping portion, a cap cleaning end provided at a first end of the body portion, the cap cleaning end including a cap cavity having a bottom surface and an inner wall surface, an internal thread cleaning end provided at a second end of the body portion, the internal thread cleaning end including a thread cavity having a cavity depth and a base surface, a longitudinal axis extending from the cap cleaning end of the sealing connector to the internal thread cleaning end of the sealing connector, the cavity depth of the internal thread cleaning end is adapted to engage a plurality of female threads of the threaded connector port. The location tube is aligned with the longitudinal axis of the sealing connector and coupled to the base surface of the thread cavity, the location tube has a length equal to or greater than the cavity depth. The inner foam pad covers the inner wall surface of the cap cavity and the bottom surface of the cap cavity, and the inner foam pad has a predetermined thickness adapted to clean a plurality of male threads on a threaded connector port cap. The outer foam sleeve has a tubular portion and a flange portion, the tubular portion has an interior surface and an exterior surface, the flange portion has an interior surface and an exterior surface, the exterior surface of the tubular portion is adjacent to the exterior surface of the flange portion, the interior surface of the tubular portion is coupled to the location tube and the interior surface of the flange portion is coupled to the base surface of the thread cavity, and the exterior surface of the tubular portion has a predetermined diameter such that, upon rotating the body portion radially about the longitudinal axis of the sealing connector, the outer foam sleeve is forced outwardly into close contact with the female threads of the threaded connector port and the inner foam pad is forced inwardly into close contact with the male threads of the threaded connector port cap.

In accordance with another exemplary aspect of the present disclosure, which may be used in combination with any one or more of the preceding aspects, the inner foam pad of the cap cavity includes a tubular foam protrusion aligned with the longitudinal axis of the sealing connector adapted to clean a cavity of the threaded connector port cap.

In accordance with another exemplary aspect of the present disclosure, which may be used in combination with any one or more of the preceding aspects, the location tube has an interior surface adapted to clean an exterior surface of a bore channel within the threaded connector port.

In accordance with another exemplary aspect of the present disclosure, which may be used in combination with any one or more of the preceding aspects, a cleaning system includes a strip of disposable containers, each disposable container includes a basin, a removable closure lid, and a cleaning apparatus. The cleaning apparatus includes a sealing connector, a location tube, an inner foam pad, and an outer foam sleeve. The basin has a cavity with an opening, the cavity is at least partially filled with a wetting fluid. The removable closure lid is attached to the basin and adapted to cover the opening of the cavity. The sealing connector is provided inside the cavity of the basin, the sealing connector includes a body portion including a gripping portion, a cap cleaning end provided at a first end of the body portion, the cap cleaning end includes a cap cavity having a bottom surface and an inner wall surface, an internal thread cleaning end provided at a second end of the body portion, the internal thread cleaning end including a thread cavity having a cavity depth and a base surface, a longitudinal axis extending from the cap cleaning end of the sealing connector to the internal thread cleaning end of the sealing connector, the cavity depth of the internal thread cleaning end is adapted to engage a plurality of female threads of the threaded connector port. The location tube is aligned with the longitudinal axis of the sealing connector and coupled to the base surface of the thread cavity, the location tube has a length equal to or greater than the cavity depth. The inner foam pad covers the inner wall surface of the cap cavity and the bottom surface of the cap cavity, and the inner foam pad has a predetermined thickness adapted to clean a plurality of male threads on a threaded connector port cap. The outer foam sleeve has a tubular portion and a flange portion, the tubular portion has an interior surface and an exterior surface, the flange portion has an interior surface and an exterior surface, the exterior surface of the tubular portion is adjacent to the exterior surface of the flange portion, the interior surface of the tubular portion is coupled to the location tube and the interior surface of the flange portion is coupled to the base surface of the thread cavity, and the exterior surface of the tubular portion has a predetermined diameter such that, upon rotating the body portion radially about the longitudinal axis of the sealing connector, the outer foam sleeve is forced outwardly into close contact with the plurality of female threads of the threaded connector port and the inner foam pad is forced inwardly into close contact with the plurality of male threads of the threaded connector port cap.

In accordance with another exemplary aspect of the present disclosure, which may be used in combination with any one or more of the preceding aspects, a sealing apparatus includes a disposable liner and a placement tool. The disposable liner includes two locator flaps, a top side and a bottom side, a longitudinal axis extending from the top side of the disposable liner to the bottom side of the disposable liner, a liner opening axially aligned with the longitudinal axis of the disposable liner, and a diameter equal to the distance between the two locator flaps, the two locator flaps each include an aperture, the liner opening includes a plurality of tails that are adapted to engage an exterior surface of a bore channel within the threaded connector port, and the diameter of the disposable liner is adapted to engage a plurality of female threads within the threaded connector port and the exterior surface of the bore channel within the threaded connector port, such that upon the insertion and rotation of a threaded connector port cap or a second threaded connector radially about the longitudinal axis of the disposable liner, the bottom side of the disposable liner is forced outwardly into close contact with the plurality of female threads of the threaded connector port and the exterior surface of the bore channel, and the top side is forced inwardly into close contact with the plurality of male threads of the threaded connector port cap or a second threaded connector such that the disposable liner creates a seal between the threaded connector port and the threaded connector port cap or between the threaded connector port and a second threaded connector. The placement tool has a handle body on a first end and two locator fingers on a second end, the two locator fingers each have a respective distal end, which is distally located from the handle body, and a respective proximal end, which is proximally located at the handle body, the two locator fingers have, at the respective distal ends, a separation distance greater than the diameter of the disposable liner, the two locator fingers are respectively axially aligned with the two locator flaps, the two locator fingers are adapted to engage the respective apertures of the two locator flaps in response to an inward pressure applied between the respective distal ends and proximal ends of the two locator fingers to decrease the separation distance of the locator fingers and allow positioning of the locator fingers within the apertures of the two locator flaps, the two locator fingers hold the disposable liner in tension in response to decreasing the application of the inward pressure, and the placement tool is adapted to release the disposable liner by positioning the disposable liner over a top surface of the threaded connector port, aligning the liner opening and the bore channel along the longitudinal axis of the disposable liner, and applying the inward pressure between the respective distal ends and proximal ends of the two locator fingers to decrease the separation distance of the locator fingers and allow the two locator fingers to withdraw from the apertures of the two locator flaps.

In accordance with another exemplary aspect of the present disclosure, which may be used in combination with any one or more of the preceding aspects, a sealing apparatus includes a disposable liner, a placement tool, and a disposable liner dispenser. The disposable liner includes two locator flaps, a top side and a bottom side, a longitudinal axis extending from the top side of the disposable liner to the bottom side of the disposable liner, a liner opening axially aligned with the longitudinal axis of the disposable liner, and a diameter equal to the distance between the two locator flaps, the two locator flaps each include an aperture, the liner opening includes a plurality of tails that are adapted to engage an exterior surface of a bore channel within the threaded connector port, and the diameter of the disposable liner is adapted to engage a plurality of female threads within the threaded connector port and the exterior surface of the bore channel within the threaded connector port, such that upon the insertion and rotation of a threaded connector port cap or a second threaded connector radially about the longitudinal axis of the disposable liner, the bottom side of the disposable liner is forced outwardly into close contact with the plurality of female threads of the threaded connector port and the exterior surface of the bore channel, and the top side is forced inwardly into close contact with the plurality of male threads of the threaded connector port cap or a second threaded connector such that the disposable liner creates a seal between the threaded connector port and the threaded connector port cap or between the threaded connector port and a second threaded connector. The placement tool has a handle body on a first end and two locator fingers on a second end, the two locator fingers each have a respective distal end, which is distally located from the handle body, and a respective proximal end, which is proximally located at the handle body, the two locator fingers have, at the respective distal ends, a separation distance greater than the diameter of the disposable liner, the two locator fingers are respectively axially aligned with the two locator flaps, the two locator fingers are adapted to engage the respective apertures of the two locator flaps in response to an inward pressure applied between the respective distal ends and proximal ends of the two locator fingers to decrease the separation distance of the locator fingers and allow positioning of the locator fingers within the apertures of the two locator flaps, the two locator fingers hold the disposable liner in tension in response to decreasing the application of the inward pressure, and the placement tool is adapted to release the disposable liner by positioning the disposable liner over a top surface of the threaded connector port, aligning the liner opening and the bore channel along the longitudinal axis of the disposable liner, and applying the inward pressure between the respective distal ends and proximal ends of the two locator fingers to decrease the separation distance of the locator fingers and allow the two locator fingers to withdraw from the apertures of the two locator flaps. The disposable liner dispenser includes a frame, a roller bar, and a liner reel. The roller bar defines a second longitudinal axis for receiving a liner reel, the liner reel includes a plurality of disposable liners attached to a leading disposable liner to be dispensed, and the plurality of disposable liners are separated by perforated edges.

In accordance with another exemplary aspect of the present disclosure, which may be used in combination with any one or more of the preceding aspects, a method for cleaning a threaded connector port includes attaching a disposable foam platform to the cleaning apparatus, moistening the disposable foam platform with wetting fluid, inserting the cleaning apparatus into the threaded connector port, rotating the cleaning apparatus about the longitudinal axis relative to the threaded connector port, while rotating, applying pressure to the gripping arms of the cleaning apparatus, removing the cleaning apparatus from the threaded connector port, removing and discarding the used disposable foam platform, positioning a disposable liner within the threaded connector port, and inserting the threaded connector port cap or a second threaded connector into the threaded connector port.

In accordance with another exemplary aspect of the present disclosure, which may be used in combination with any one or more of the preceding aspects, a method for cleaning a threaded connector port includes unscrewing the threaded connector port cap with the pair of cleats included on the handle body of the cleaning apparatus, moistening the disposable foam platform with wetting fluid, inserting the cleaning apparatus into the threaded connector port, rotating the cleaning apparatus about the longitudinal axis relative to the threaded connector port, removing the cleaning apparatus from the threaded connector port, positioning a disposable liner within the threaded connector port, and insert threaded connector port cap or second threaded connector into the threaded connector port.

In accordance with another exemplary aspect of the present disclosure, which may be used in combination with any one or more of the preceding aspects, a method for cleaning a threaded connector port includes removing a cleaning apparatus from a disposable container, inserting the internal thread cleaning end of the sealing connector of the cleaning apparatus onto the threaded connector port, inserting the threaded connector port cap inside the cap cleaning end of the sealing connector, rotating the cleaning apparatus radially about the longitudinal axis, removing the cleaning apparatus, positioning a disposable liner within the threaded connector port, and inserting a threaded connector port cap or second threaded connector into the threaded connector port.

In accordance with another exemplary aspect of the present disclosure, which may be used in combination with any one or more of the preceding aspects, a method for sealing a threaded connector port includes grabbing a disposable liner with the placement tool, positioning the disposable liner over the threaded connector port, releasing the disposable liner at the top surface of the threaded connector port, sealing the threaded connector port by screwing in a threaded connector or a threaded connector port cap, using the threaded connector port, and removing and disposing of the disposable liner.

Additional features and advantages of the disclosed system, method, and apparatus are described in, and will be apparent from, the following Detailed Description and the Figures.

BRIEF DESCRIPTION OF THE FIGURES

FIG. 4A is a perspective view of an example cleaning apparatus, according to an example embodiment of the present disclosure.

FIG. 4B is a side view of an example cleaning apparatus, according to an example embodiment of the present disclosure.

FIG. 4C is an enlarged view of an example cleaning arm of a cleaning apparatus, according to an example embodiment of the present disclosure.

FIG. 4D is a side view of an example cleaning system, according to an example embodiment of the present disclosure.

FIG. 4E is a side view of an example cleaning system, according to an example embodiment of the present disclosure.

FIG. 4F is a perspective view of an example cleaning system, according to an example embodiment of the present disclosure.

DETAILED DESCRIPTION OF EXAMPLE EMBODIMENTS

Figure 1:
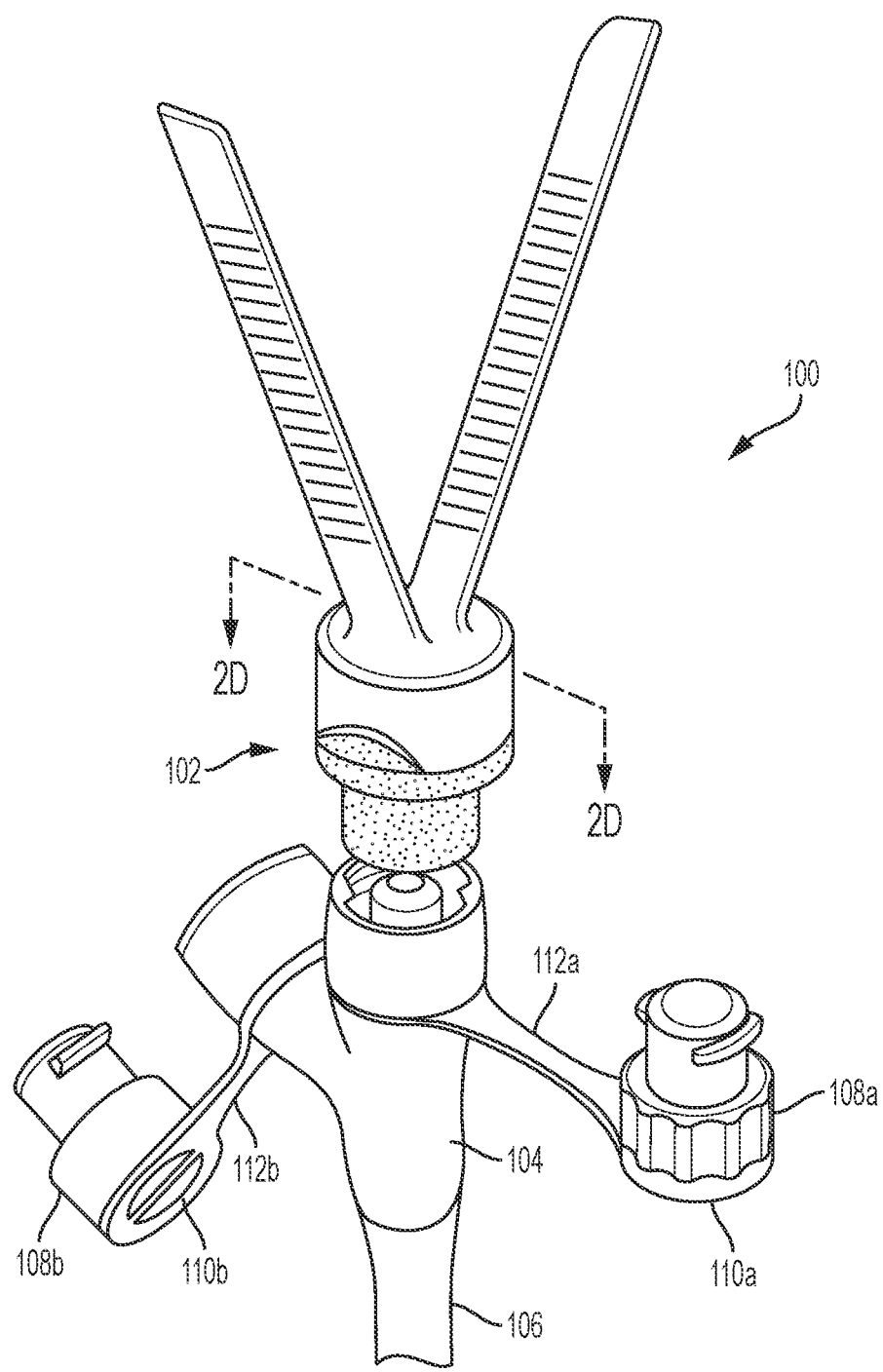
FIG. 1 is a perspective view of an example cleaning system, according to an example embodiment of the present disclosure.

A perspective view of an example cleaning system 100 is illustrated in FIG. 1. The illustrated cleaning system 100 includes a cleaning apparatus 102 and a threaded connector port 104. The cleaning apparatus 102 includes a disposable foam platform (described in more detail below), which is depicted with dotted shading to illustrate an exemplary texture of the disposable foam platform. It should be understood that the disposable foam platform and/or other embodiments with foam materials need not be depicted with dotted shading. The threaded connector port 104 is connected to a feeding tube 106. The threaded connector port 104 may also include one or more threaded connector port caps 108a and 108b. The threaded connector port caps 108a and 108b may have a smooth exterior (e.g., 108b) or may have a textured exterior that includes knurling and/or other gripping elements (e.g., 108a). As described herein, the threaded connector port caps 108a and 108b may be referred to generally as 108. Each threaded connector port cap 108 includes a top surface 110a and 110b, hereinafter 110. The threaded connector port 104 may also include one or more ring connectors 112a and 112b, hereinafter 112. The ring connectors 112 enable the threaded connector port caps 108 to swing or rotate circumferentially around the threaded port connector 104, thus facilitating movement and positioning of the threaded port connector caps 108 for better access by a clinician or patient. Moreover, the ring connectors 112 ensure that the threaded port connector caps 108 remain with the threaded connector port 104. It should be appreciated that the threaded port connector caps 108 may be attached with another suitable connector to be attached from the threaded connector port 104 to the threaded connector port caps 108. Additionally, the threaded port connector caps 108 may not be attached to the threaded port connector 104. The threaded connector port 104 may be connected to many different types of medical tubes, a feeding tube 106 has been shown only for visual reference.

Figure 2A:
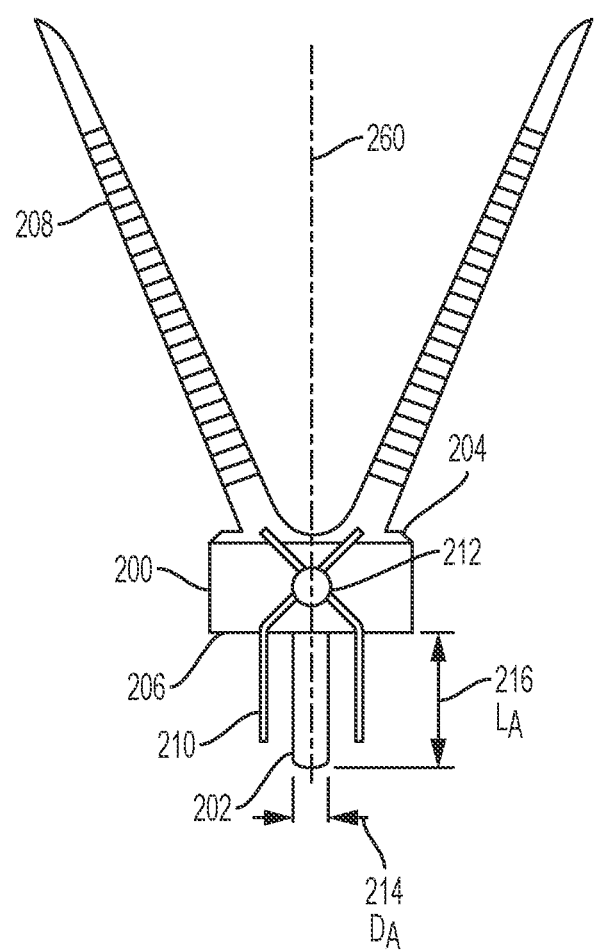
FIG. 2A is a side view of an example handle body and alignment peg of a cleaning apparatus, according to an example embodiment of the present disclosure.

FIG. 2A is a side view of an example handle body 200 and an alignment peg 202 of a cleaning apparatus 102, according to an example embodiment of the present disclosure. The handle body 200 includes a first end 204 and a second end 206. A pair of gripping arms 208 extends upward from the first end 204 of the handle body 200. The pair of gripping arms 208 may be textured or include additional gripping members (not pictured) to allow for improved grip and manipulation of the cleaning apparatus 102. A pair of cleaning arms 210 extends downward from the second end 206 of the handle body 200. The handle body 200, the pair of cleaning arms 210, and the pair of gripping arms 208 may be made of a flexible material (e.g., polyethylene). For example, the handle body 200, the pair of cleaning arms 210, and the pair of gripping arms 208 may be made of the same material, in a single mold, or multiple materials from several molds. The construction may include one or more materials including, polyethylene, silicon, thermoplastic, or the like, and may also be latex-free. Additionally, the pair of gripping arms 208 may be made of a different material than the pair of cleaning arms 210. For example, the pair of cleaning arms 210 may be made of metal, such as stainless steel, or the like. The pair of cleaning arms 210 is pivotally connected to the pair of gripping arms 208 by a pivot pin 212 enclosed within the handle body 200. In an example embodiment, the pair of cleaning arms 210 and the pair gripping arms 208 may be molded as one piece that meet at a pivot point. In an example embodiment, the pair of cleaning arms 210 and the pair of gripping arms 208 may be coupled in spring tension at a pivot point. For example, the pair of cleaning arms 210 may be made of a metal wire that is coiled to form a spring (not pictured) at a pivot point and that continues into the pair of gripping arms 208. The wire portion that continues into the pair of gripping arms 208 may be coated with a softer material to allow for easier and more comfortable handling by the clinician.

The handle body 200 has a longitudinal axis 260 that extends from the first end 204 of the handle body 200 to the second end 206 of the handle body 200. The alignment peg 202 is aligned with the longitudinal axis 260 of the handle body 200 and coupled to the second end 206 of the handle body 200. The alignment peg 202 may be molded plastic of a different material than the handle body 200 and may be secured to the handle body 200 with an adhesive or other suitable fastening means to ensure that the handle body 200 and the alignment peg 202 are operatively coupled. Also, the alignment peg 202 may be molded as part of the same piece as the handle body 200. The alignment peg 202 has an outside diameter $(D_A)$ 214 and a length $(L_A)$ 216. The length $(L_A)$ 216 of the alignment peg 202 may extend beyond the pair of cleaning arms 210 to allow the clinician to align the entire length of a foam platform (described below) within the threaded connector port 104. It should be appreciated that it may be more difficult for a clinician to articulate the placement of the cleaning apparatus 102 within the threaded connector port 104 if the alignment peg 202 is considerably shorter than the length of the cleaning arms 210, however, in an example embodiment, the length $(L_A)$ 216 of the alignment peg 202 may be shorter than the pair of cleaning arms 210. In an example embodiment, a hollow location tube may also be used.

Figure 2B:
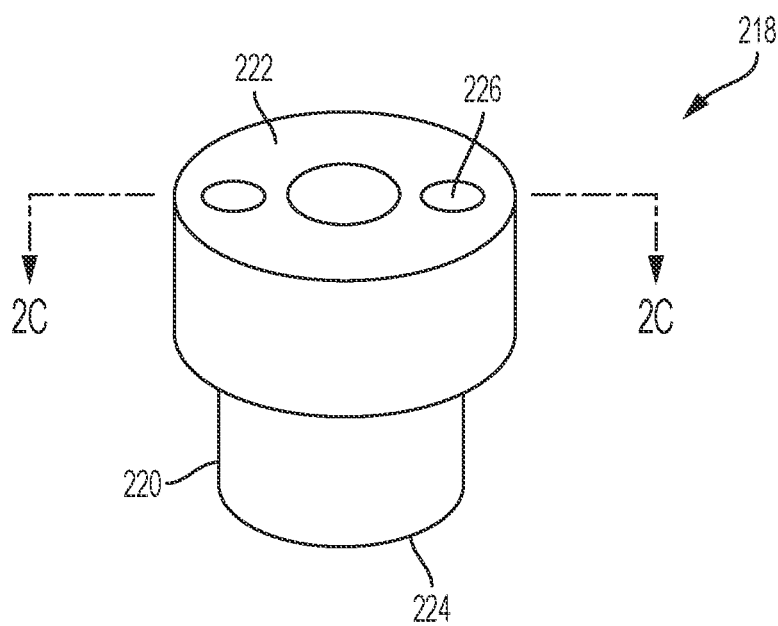
FIG. 2B is a perspective view of an example disposable foam platform, according to an example embodiment of the present disclosure
Figure 2C:
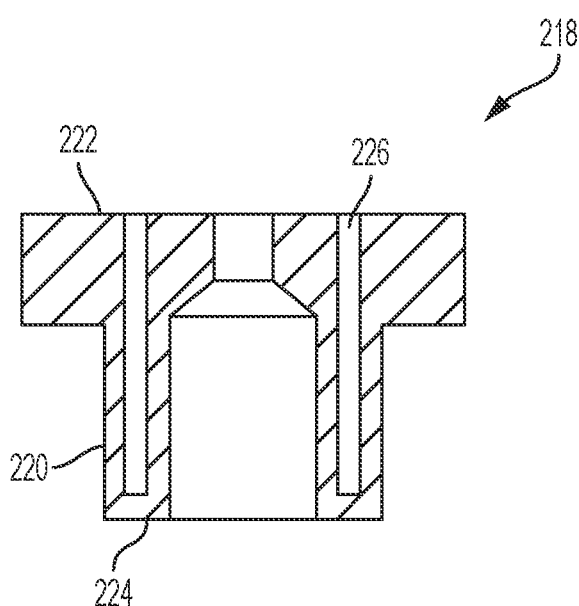
FIG. 2C is a cross-sectional view of an example disposable foam platform, according to an example embodiment of the present disclosure.

FIG. 2B is a perspective view of an example disposable foam platform 218, according to an example embodiment of the present disclosure. A cross-sectional view of the disposable foam platform 218 is illustrated in FIG. 2C, taken along line 2C-2C in FIG. 2B. As shown in FIG. 2B, the disposable foam platform 218 includes a tubular hollow portion 220, an attachment end 222, and a cleaning end 224. The disposable foam platform 218 also has a pair of cavities 226 adapted to receive the pair of cleaning arms 210. In an example embodiment, the handle body 200 may include multiple pairs of cleaning arms that are received by a larger pair of cavities or multiple pairs of cavities on the disposable foam platform 218. For example, the pair of cavities 226 may be adapted to receive multiple pairs of cleaning arms. The disposable foam platform 218 may also include multiple pairs of cavities where each pair of cavities is adapted to receive the respective pair of cleaning arms. The disposable foam platform 218 may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities.

Figure 2D:
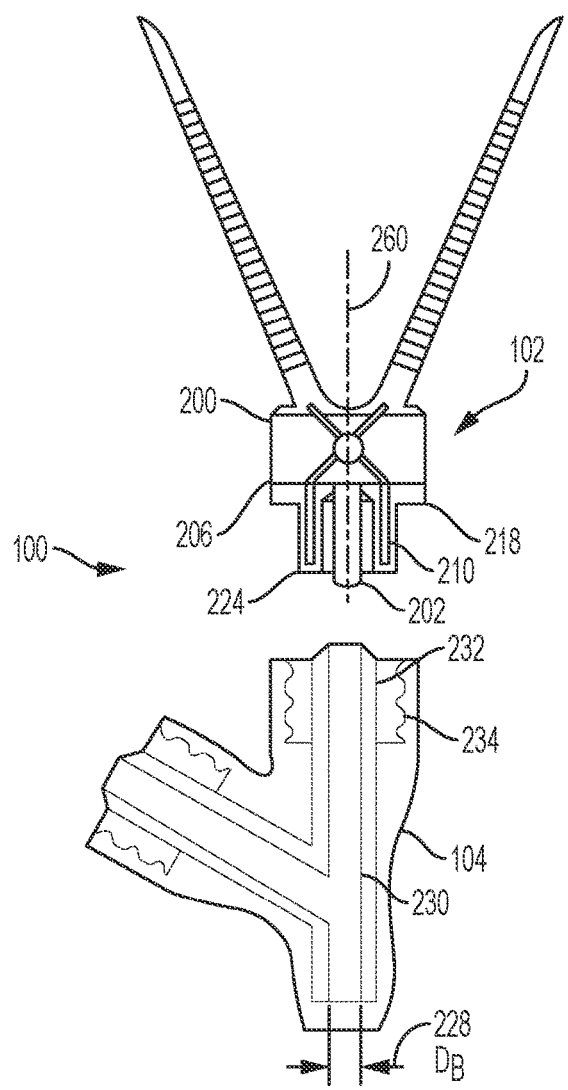
FIG. 2D is a cross-sectional view of an example cleaning system, according to an example embodiment of the present disclosure.

FIG. 2D is a cross-sectional view, taken along line 2D-2D of FIG. 1, of an example cleaning system 100, according to an example embodiment of the present disclosure. As shown in FIG. 2D, cleaning system 100 includes a cleaning apparatus 102 and a threaded connector port 104. The cleaning apparatus 102 includes a handle body 200, a disposable foam platform 218, and an alignment peg 202. The disposable foam platform 218 is coupled to the second end 206 of the handle body 200. As shown in FIG. 2D, the alignment peg 202 has an outside diameter $(D_A)$ 214 smaller than an internal diameter $(D_B)$ 228 of a bore channel 230 running through the threaded connector port 104. The bore channel 230 has an exterior surface 232. The threaded connector port 104 includes a plurality of female threads 234. In an example embodiment, the cleaning apparatus 102 may include a foam platform that is permanently affixed to the second end 206 of the handle body 200. For example, the foam platform may be designed of a material that is suitable for extended use (e.g., multiple cleanings).

Figure 2E:
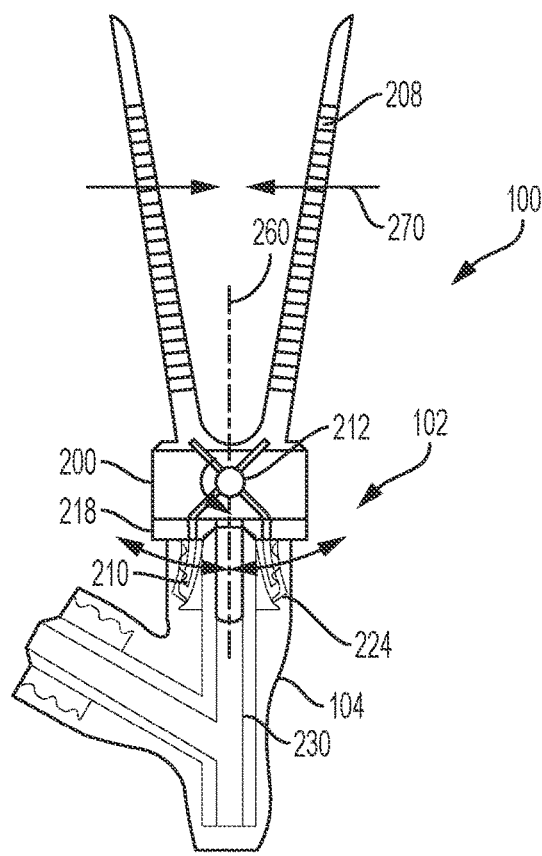
FIG. 2E is a cross-sectional view of an example cleaning system, according to an example embodiment of the present disclosure.

FIG. 2E is a cross-sectional view, taken along line 2D-2D of FIG. 1, of an example cleaning system 100, according to an example embodiment of the present disclosure. As shown in FIG. 2E the pair of cleaning arms 210 of the handle body 200 is urged apart by applying pressure 270 at the pair of gripping arms 208 in an inward direction towards the longitudinal axis 260 of the handle body 200. The pressure 270 is transferred through the pivot pin 212 to urge the pair of cleaning arms 210 apart. It should be appreciated that the pair of cleaning arms 210 and the pair of gripping arms 208 may interact like a pair of expansion pliers, as described, where the pair of cleaning arms 210 is urged apart in response to an inward pressure 270 being applied to the pair of gripping arms 208, however, the pair of cleaning arms 210 and the pair of gripping arms 208 may also interact like a pair of conventional pliers, where the pair of cleaning arms 210 is urged together in response to an inward pressure 270 being applied to the pair of gripping arms 208. In either case, the clinician may actuate the pair of cleaning arms 210 to move inward or outward to assist in cleaning several surfaces within the threaded connector port 104 (e.g., the exterior surface 232 of the bore channel 230 and the plurality of female threads 234). The cleaning apparatus 102 is aligned within the threaded connector port 104 by inserting the alignment peg 202 into the bore channel 230 of the threaded connector port 104.

As shown in FIG. 2E, the cleaning end 224 of the disposable foam platform 218 is adapted to clean the plurality of female threads 234 of the threaded connector port 104 when the alignment peg 202 is inserted into the bore channel 230 of the threaded connector port 104 and the handle body 200 is rotated radially about the longitudinal axis 260 relative to the threaded connector port 104. The cleaning end 224 of the disposable foam platform 218 is also adapted to clean the exterior surface 232 of the bore channel 230 when the alignment peg 202 is inserted into the bore channel 230 of the threaded connector port 104. The clinician may apply pressure 270 to the pair of gripping arms 208 as needed to ensure that all the surfaces of interest within the threaded connector port 104 are cleaned. In an example embodiment, the alignment peg 202 may be textured or coated with an appropriate material suitable for cleaning the bore channel 230 of the threaded connector port 104. Additionally, the alignment peg 202 may be a hollow tube adapted to fit over the exterior surface 232 of the bore channel 230, and may be further adapted to clean the exterior surface 232 of the bore channel 230 by having a textured inner surface or by being coated with a suitable cleaning material. In an example embodiment, the cleaning apparatus 102 may include both the alignment peg 202 (e.g., as illustrated in FIGS. 2D and 2E) and the hollow tube adapted to fit over the exterior surface 232 of the bore channel 230. For example, the alignment peg 202 and the hollow tube may both assist a clinician with aligning the cleaning apparatus 102 with the threaded connector port 104.

Figure 2F:
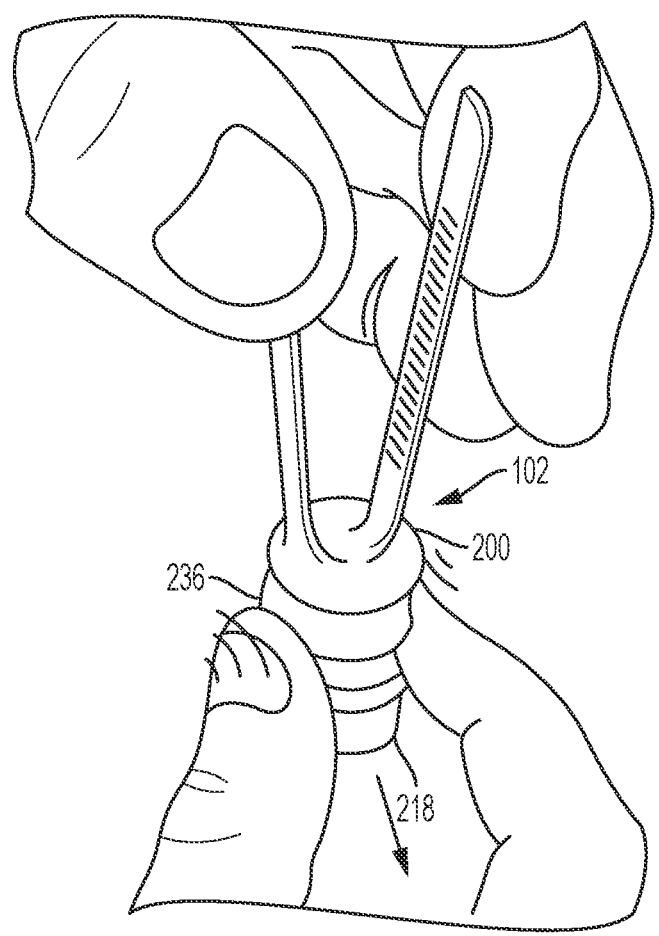
FIG. 2F is a perspective view of an example cleaning apparatus, according to an example embodiment of the present disclosure.

FIG. 2F is a perspective view of an example cleaning apparatus 102, according to an example embodiment of the present disclosure. As shown in FIG. 2F the handle body 200 includes at least two scallops 236 that are adapted to assist in the removal of the disposable foam platform 218 from the handle body 200. For example, the at least two scallops 236 on the handle body 200 may allow the clinician's thumb and finger to be placed on the edge of the disposable foam platform 218, advantageously providing the clinician with increased leverage and grip for removing the disposable foam platform 218. Accordingly, a clinician may advantageously remove the disposable foam platform 218 with his or her hand without having to use a separate tool. Further, in an example embodiment, the disposable foam platform 218 may include structural features adapted to assist with the removal of the disposable foam platform 218 by the clinician. For example, the disposable foam platform 218 may include bumps, ridges, indentations, or additional gripping members adapted to assist with the removal of the disposable foam platform 218. It should be appreciated that the structural features adapted to assist with the removal of the disposable foam platform 218 may be made of the same material of the disposable foam platform 218, or the structural features may be made of a different material and secured to the disposable foam platform 218 with an adhesive or other suitable fastening means to ensure that the disposable foam platform 218 and the structural features are operatively coupled.

Figure 3:
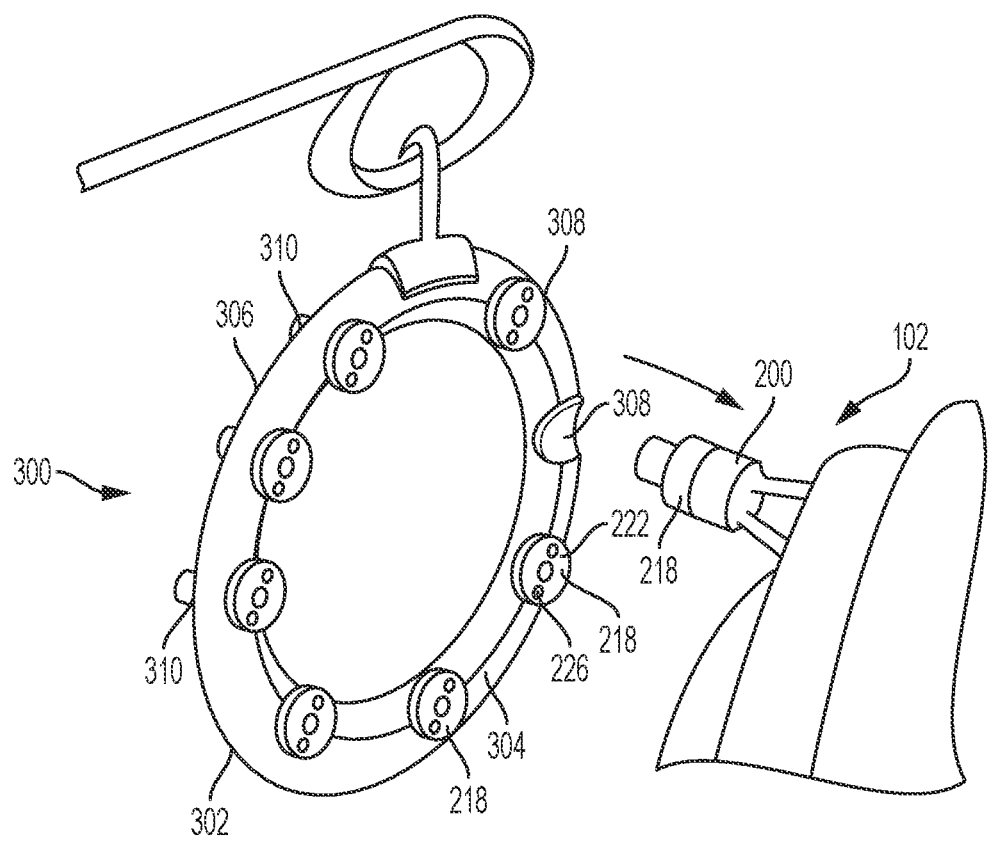
FIG. 3 is a perspective view of an example cleaning assembly, according to an example embodiment of the present disclosure.

FIG. 3 is a perspective view of an example cleaning assembly 300, according to an example embodiment of the present disclosure. As shown in FIG. 3, the cleaning assembly 300 comprises a foam platform dispenser housing 302. The foam platform dispenser housing 302 has a front side 304 and a back side 306. The front side 304 has a plurality of attachment end openings 308. The back side 306 has a plurality of cleaning end openings 310. The plurality of attachment end openings 308 are axially aligned to the plurality of cleaning end openings 310. The plurality of openings (308, 310) is adapted for receiving disposable foam platforms 218. For example, the openings may be sized in a way to hold the disposable foam platforms 218 in compression, or the openings may utilize another securing or fastening means to ensure that the disposable foam platforms 218 remain in the dispenser housing 302 until the clinician decides to remove a disposable foam platform 218. In an example embodiment, the back side 306 of the foam platform dispenser housing 302 may be solid without any cleaning end openings 310 or the foam platform dispenser housing 302 may have a cap or lid (not pictured) which covers the cleaning end openings 310. The cap or lid may be permanently affixed to foam platform dispenser housing 302, or cap or lid may be adapted to be opened or removed to enable access to the cleaning ends 224 of the disposable foam platforms 218. For example, the cleaning ends 224 of the disposable foam platforms 218 may sit inside the foam platform dispenser housing 302 so that the cleaning ends 224 are shielded from the outside environment.

The cleaning apparatus 102 and the foam platform dispenser housing 302 are adapted to cooperate in dispensing the disposable foam platform 218 from the foam platform dispenser housing 302 to the cleaning apparatus 102. The handle body 200 of the cleaning apparatus 102 is axially aligned with one of the plurality of attachment end openings 308, and the second end 206 of the handle body 200 is pressed onto the attachment end 222 of the disposable foam platform 218 to engage the pair of cavities 226 of the attachment end 222 of the disposable foam platform 218 being coupled to the second end 206 of the handle body 200. It should be appreciated that the dispenser housing 302 allows a clinician to attach a new disposable foam platform 218 to the handle body 200 without having to touch the foam platform 218 with his or her hands, thereby reducing the risk of contaminating the disposable foam platform 218. A suitable adhesive or fastening mechanism may be used to operatively couple the disposable foam platform 218 to the handle body 200. For example, the disposable foam platforms 218 may include a pre-applied adhesive that would bond to the handle body 200 once the clinician pressed the handle body 200 onto the attachment end 222 of the disposable foam platform 218. Furthermore, the handle body 200 may include a fastening mechanism such as a plastic lip with plastic spines that allow the disposable foam platform 218 to slide onto the handle body 200, but the spines prevent the disposable foam platform 218 from easily releasing from the handle body 200 because the spines engage the material of the disposable foam platform 218 and provide resistance to removing the foam platform 218 from the handle body 200. Additionally, the handle body 200 may include a fastening mechanism such as hooks included on the handle body 200 that engage loops on the disposable foam platform 218 or engage the material or other structural features of the disposable foam platform 218 to provide resistance to removing the disposable foam platform 218 from the handle body 200.

FIG. 4A is a perspective view and FIG. 4B is a side view of an example cleaning apparatus 401, according to an example embodiment of the present disclosure. The cleaning apparatus 401 comprises a handle body 402 and a first plurality of foam pads 404 (e.g., 404a, 404b, and 404c). The handle body 402 has a first end 406 and a second end 408. A longitudinal axis 480 extends from the first end 406 of the handle body 402 to the second end 408 of the handle body 402. The first end 406 of the handle body 402 includes a grip portion 410. The grip portion 410 may be textured or include additional gripping members (not pictured) to allow for improved grip and manipulation of the cleaning apparatus 401. The second end 408 of the handle body 402 includes two cleaning arms 412. The two cleaning arms 412 each have a proximal end 414 and a terminal end 416. The terminal end 416 of each cleaning arm 412 is distally located from the handle body 402. Each of the terminal ends 416 of the cleaning arms 412 has an outward facing flange 418. It should be appreciated that the thickness of the cleaning arms 412 may vary to provide a suitable level of flexibility and rigidity. In an example embodiment, the two cleaning arms 412 may have different lengths enabling them to engage offset threads of a threaded connector port 104 while maintaining an orientation directly in line with the longitudinal axis 480. The handle body 402 may be made of a flexible material (e.g., polyethylene). For example, the handle body 402, the grip portion 410, and the two cleaning arms 412 may be made of the same material, in a single mold, or multiple materials from several molds. The construction may include one or more materials including, polyethylene, silicon, thermoplastic, or the like, and may also be latex-free.

FIG. 4C is an enlarged view of a cleaning arm 412 of an example cleaning apparatus 401, according to an example embodiment of the present disclosure. Each cleaning arm 412 has an outward facing flange 418 which has a height ($H_F$) 420 and width ($W_F$) 422. In an example embodiment, the length of the cleaning arms 412, the height ($H_F$) 420 of the outward facing flange 418, and the width ($W_F$) 422 of the outward facing flange 418 may vary depending on the application. Each of the two cleaning arms 412 include a first outer surface 424, a second outer surface 426, and a third outer surface 428. The first outer surface 424 extends from the proximal end 414 of the cleaning arms 412 to the terminal end 416 of the cleaning arms 412. The second outer surface 426 extends from the terminal end 416 of the cleaning arms 412 along the width ($W_F$) 422 of the outward facing flange 418. The third outer surface 428 extends from the second outer surface 426 along the height ($H_F$) 420 of the outward facing flange 418. The first plurality of foam pads 404a, 404b, and 404c are respectively coupled to the first outer surface 424, the second outer surface 426, and third outer surface 428 of each of the cleaning arms 412. Hereinafter, the plurality of foam pads 404a, 404b, and 404c are generally referred to as 404. In another embodiment, the cleaning apparatus 401 includes a second plurality of foam pads 430a and 430b, hereinafter generally referred to as 430. Each foam pad of the second plurality of foam pads 430 is respectively coupled to a first inner surface 432 of the cleaning arms 412 and a second inner surface 434 of the cleaning arms 412. The first inner surface 432 extends from the proximal end 414 of the cleaning arms 412 to the terminal end 416 of the cleaning arms 412. The second inner surface 434 extends from the terminal end 416 of the cleaning arms 412 along the width ($W_F$) 422 of the outward facing flange 418. In an example embodiment, the first plurality of foam pads 404 and/or the second plurality of foam pads 430 may extend the entire length of the cleaning arms 412 or just a portion of the length of the cleaning arms 412 depending on the application. The first and/or second plurality of foam pads (404, 430) may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities. Furthermore, in an example embodiment of the present disclosure, the cleaning arms 412 may be covered with foam sleeves (not pictured) that slide over each cleaning arm 412. In another example embodiment, the cleaning arms 412 may be textured or coated with a suitable material to clean the respective female threads 436 of the threaded connector port 104.

The cleaning apparatus 401 may include an alignment peg (not pictured), similar to alignment peg 202, which may be textured or coated with a suitable material to clean the bore channel 230 of the threaded connector port 104. Additionally, the alignment peg (not pictured) may be a hollow tube adapted to fit over the exterior surface 232 of the bore channel 230, and may be further adapted to clean the exterior surface 232 of the bore channel 230 by having a textured inner surface or by being coated with a suitable cleaning material. In an example embodiment, the handle body 402 may include one cleaning arm. For example, the cleaning apparatus 401 may include an alignment peg or tube and a handle body 402 that includes one cleaning arm. In an example embodiment, the handle body 402 may include three or more cleaning arms 412. For example, the three or more cleaning arms 412 may be spaced equidistant from each other. In another example embodiment, the handle body 402 may include two or more pairs of cleaning arms 412. Each pair of the two or more pairs of cleaning arms 412 may be tightly grouped together enabling the cleaning apparatus 401 to have a flatter profile than an embodiment including three or more cleaning arms 412 that are spaced equidistant about the handle body 402.

FIG. 4D and FIG. 4E are cross-sectional views of an example cleaning system 400, according to an example embodiment of the present disclosure. The height ($H_F$) 420 and the width ($W_F$) 422 of the outward facing flange 418 are adapted to engage a respective female thread 436 of the threaded connector port 104. The first plurality of foam pads 404 are adapted to clean the respective female threads 436 of the threaded connector port 104 as the outward facing flanges 418 maintain an outward pressure 470 on the first plurality of foam pads 404 while the handle body 402 is inserted into the threaded connector port 104 and rotated radially about the longitudinal axis 480 of the handle body 402. In an example embodiment, the handle body 402 may be molded such that the cleaning arms 412 are in a pre-tension state, thereby creating an outward pressure 470 against the interior surfaces of the threaded connector port 104. Also, the female threads 436 may be larger than the height ($H_F$) 420 and/or the width ($W_F$) 422 of the outward facing flange 418, but smaller than the plurality of foam pads 404 in an uncompressed state. Accordingly, the plurality of foam pads 404 may be sized to fit tightly into the female threads 436 and exert pressure in all directions on the female threads 436 when in a compressed state. Accordingly, a clinician may advantageously insert the handle body 402 into a threaded connector port 104 and rotate the apparatus radially about the longitudinal axis 480 without having to actuate the cleaning arms 412.

In another example embodiment, in FIG. 4F, the handle body 402 of the cleaning apparatus 401 includes a pair of cleats 438. The pair of cleats 438 is adapted to engage a top surface 110 of a threaded connector port cap 108 to assist in unscrewing the threaded connector port cap 108. It should be appreciated that there may be more than one pair of cleats 438 adapted to assist in unscrewing the threaded connector port cap 108. The pair of cleats 438 may be made of the same material, in a single mold, or multiple materials from several molds. The construction may include one or more materials including, polyethylene, silicon, thermoplastic, or the like. The pair of cleats 438 may be made from plastic of a different material than the handle body 402 and secured to the handle body 402 with an adhesive or other suitable fastening means to ensure that the handle body 402 and the alignment pair of cleats 438 are operatively coupled.

Figure 4G:
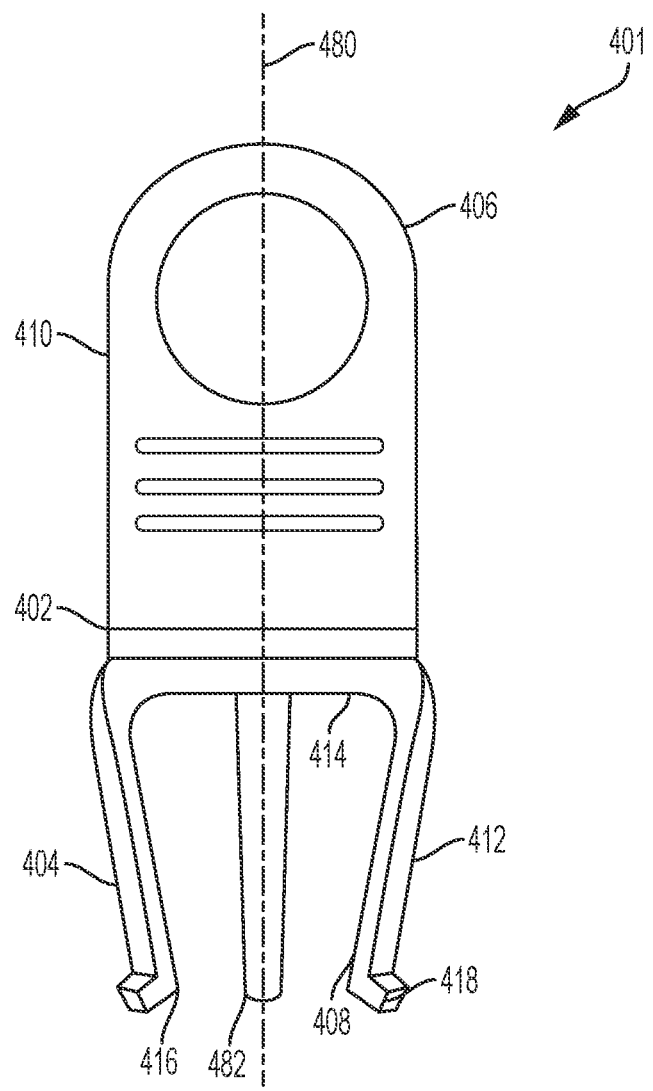
FIG. 4G is a side view of an example cleaning apparatus, according to an example embodiment of the present disclosure.

In another example embodiment, in FIG. 4G, the cleaning apparatus 401 may include an alignment peg 482. The alignment peg 482 is aligned with the longitudinal axis 480 of the handle body 402. The alignment peg 480 may be molded plastic of a different material than the handle body 402 and may be secured to the handle body 402 with an adhesive or other suitable fastening means to ensure that the handle body 402 and the alignment peg 482 are operatively coupled. Also, the alignment peg 482 may be molded as part of the same piece as the handle body 402. The alignment peg 482 has an outside diameter and a length. The length of the alignment peg 482 may extend beyond extend beyond the terminal end 416 of each cleaning arm 412. It should be appreciated that it may be more difficult for a clinician to articulate the placement of the cleaning apparatus 401 within the threaded connector port 104 if the alignment peg 482 is considerably shorter than the length of the cleaning arms 412, however, in an example embodiment, the length of the alignment peg 482 may be shorter than the cleaning arms 412. In an example embodiment, a hollow location tube may also be used.

In an example embodiment, the alignment peg 482 may be textured or coated with an appropriate material suitable for cleaning the bore channel 230 of the threaded connector port 104. Additionally, the alignment peg 482 may be a hollow tube adapted to fit over the exterior surface 232 of the bore channel 230, and may be further adapted to clean the exterior surface 232 of the bore channel 230 by having a textured inner surface or by being coated with a suitable cleaning material. In an example embodiment, the cleaning apparatus 401 may include both the alignment peg 482 (e.g., as illustrated in FIG. 4G) and the hollow tube adapted to fit over the exterior surface 232 of the bore channel 230. For example, the alignment peg 482 and the hollow tube may both assist a clinician with aligning the cleaning apparatus 401 with the threaded connector port 104.

Figure 5A:
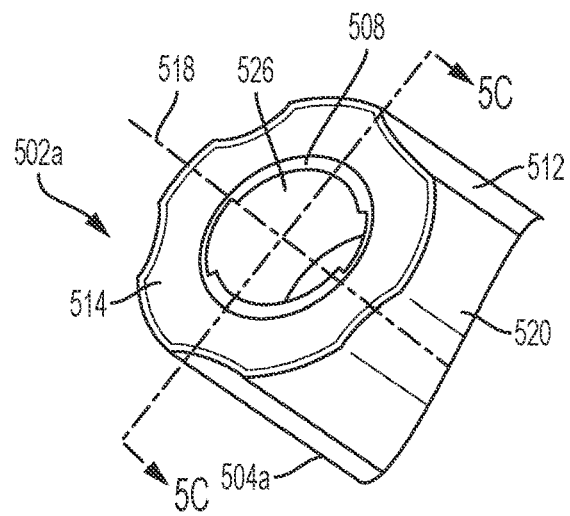
FIG. 5A is an enlarged partial view of an example cleaning apparatus, according to an example embodiment of the present disclosure.
Figure 5B:
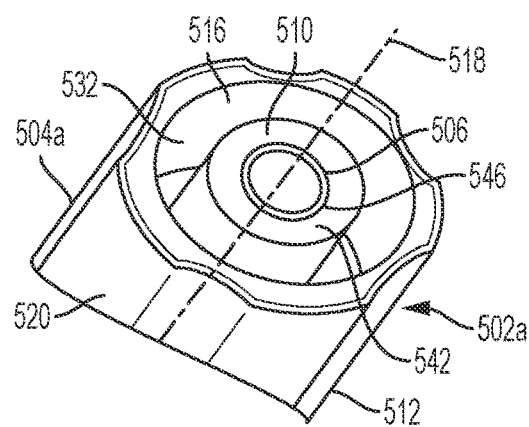
FIG. 5B is an enlarged partial view of an example cleaning apparatus, according to an example embodiment of the present disclosure.
Figure 5C:
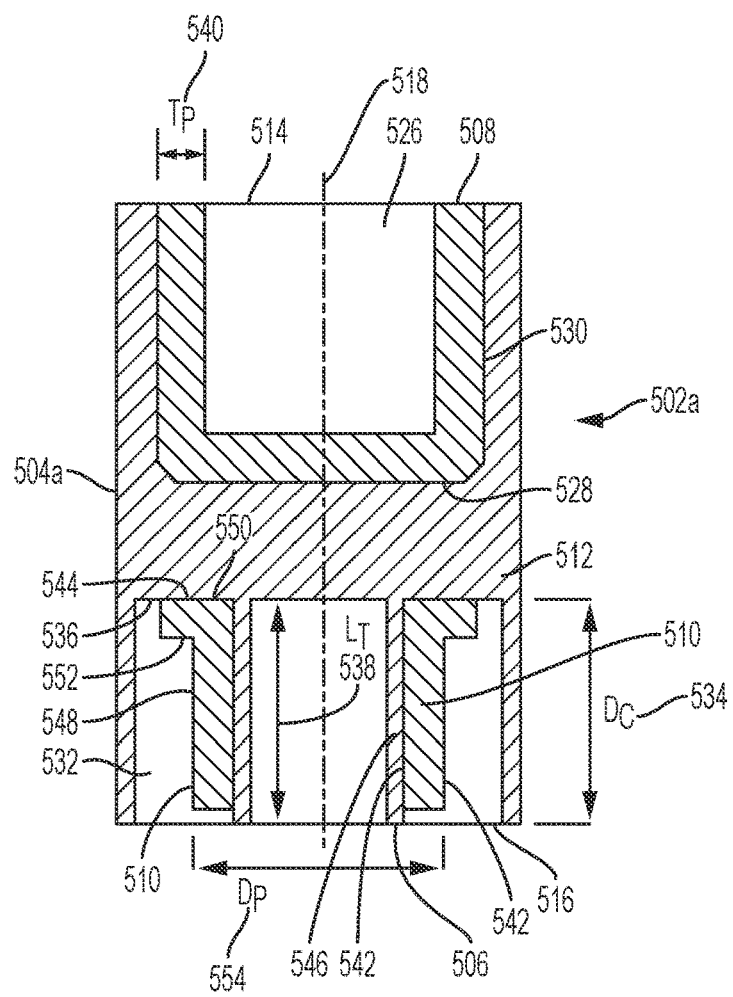
FIG. 5C is a cross-sectional view of an example cleaning apparatus, according to an example embodiment of the present disclosure.

FIGS. 5A and 5B are enlarged partial perspective views of the cleaning apparatus 502a, according to an example embodiment of the present disclosure. The cleaning apparatus 502a comprises a sealing connector 504a, a location tube 506, an inner foam pad 508, and an outer foam sleeve 510. The sealing connector 504a is shown in greater detail in FIG. 5C which depicts a cross-sectional view of the cleaning apparatus 502a, taken along line 5C-5C of FIG. 5A. The sealing connector 504a may seal a cleaning area (e.g., area between the bore channel 230 and the female threads 436 on the threaded connector port 104) to prevent foreign material from entering the threaded connector port 104 during cleaning. For example, the sealing connector 504a may fit over and around a bore channel 230 of a threaded connector port 104. Additionally, the outer foam sleeve 510 may form a seal between the cleaning area and the outside environment to prevent foreign material from entering the cleaning area during cleaning. It should be understood that the sealing connector 504a need not create an operative or hermetic seal with the threaded connector port 104. For example, the seal may act as a debris barrier. The sealing connector 504a includes a body portion 512, a cap cleaning end 514, an internal thread cleaning end 516, and a longitudinal axis 518. The body portion 512 of the sealing connector 504a includes a gripping portion 520 provided between the two ends of the sealing connector 504a. The gripping portion 520 may be textured and may include gripping members made from the same or different material than the sealing connector. The gripping portion 520 need not be textured or include gripping members. Essentially, the gripping portion 520 may merely be sufficient for a clinician to grip and use the cleaning apparatus 502a (e.g., twisting action). The cap cleaning end 514 of the sealing connector 504a is provided at one end of the body portion 512. The cap cleaning end 514 includes a cap cavity 526 having a bottom surface 528 and an inner wall surface 530. The internal thread cleaning end 516 of the sealing connector 504a is provided at the other end of the body portion 512. The internal thread cleaning end 516 includes a thread cavity 532 having a cavity depth ($D_C$) 534 and a base surface 536. The longitudinal axis 518 of the sealing connector 504a extends from the cap cleaning end 514 to the internal thread cleaning end 516 of the sealing connector 504a. The cavity depth ($D_C$) 534 of the internal thread cleaning end 516 is adapted to engage a plurality of female threads 234 of the threaded connector port 104. In an example embodiment, the cleaning apparatus 502a may also include an alignment peg similar to alignment peg 202.

Figure 5D:
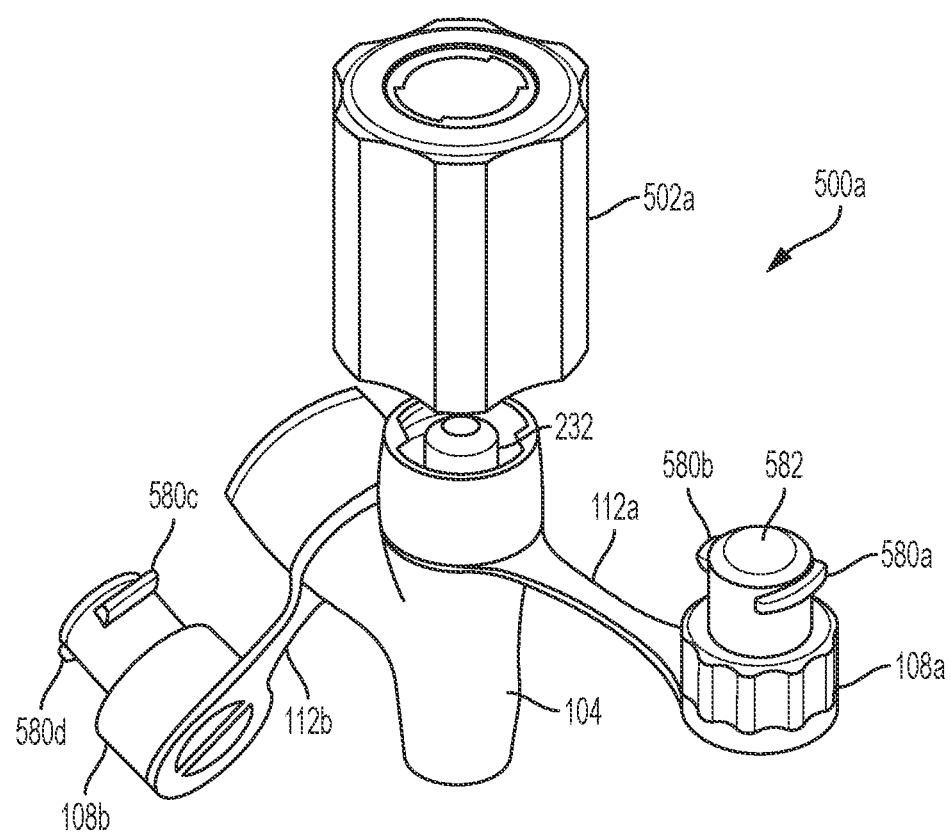
FIG. 5D is a perspective view of an example cleaning system, according to an example embodiment of the present disclosure.
Figure 5E:
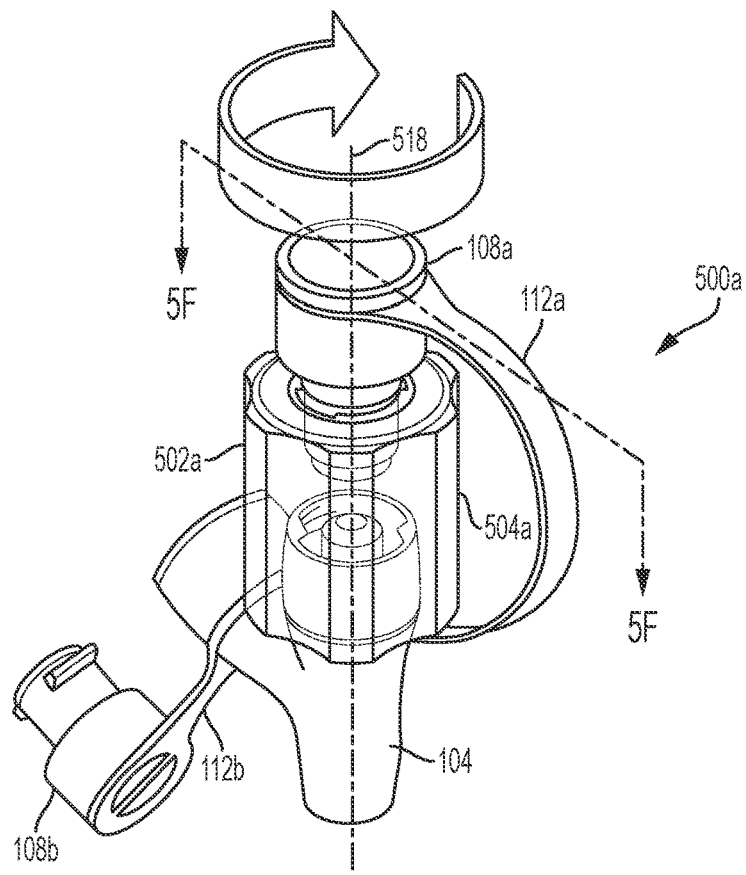
FIG. 5E is a perspective view of an example cleaning system, according to an example embodiment of the present disclosure.
Figure 5F:
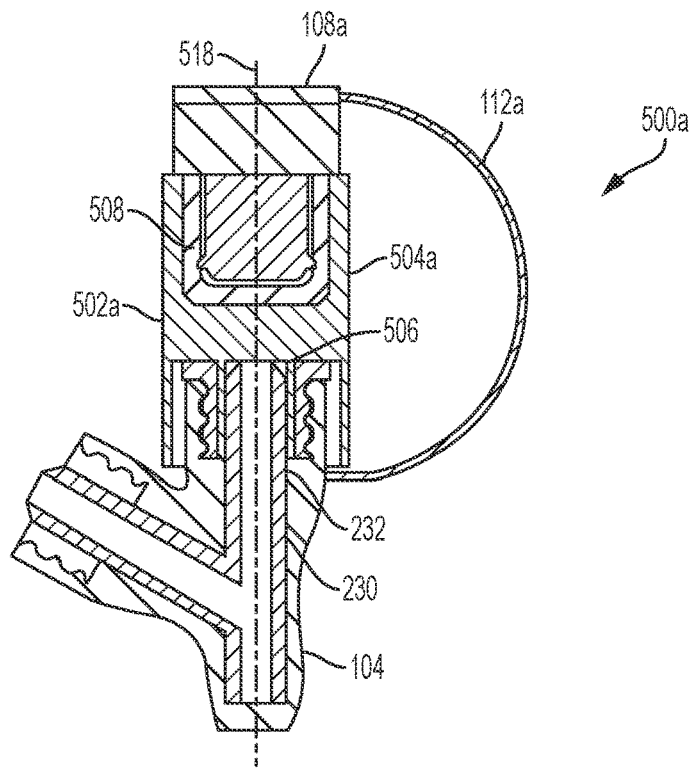
FIG. 5F is a cross-sectional view of an example cleaning system, according to an example embodiment of the present disclosure.

FIGS. 5D and 5E are perspective views of an example cleaning system 500a, according to an example embodiment of the present disclosure. A cross-sectional view of the cleaning system 500a is illustrated in FIG. 5F, taken along line 5F-5F of FIG. 5E. The cleaning system 500a includes a cleaning apparatus 502a and a threaded connector port 104. The cleaning apparatus 502a is described in FIG. 5A, FIG. 5B, and FIG. 5C. The location tube 506 of the cleaning apparatus 502a is aligned with the longitudinal axis 518 of the sealing connector 504a and coupled to the base surface 536 of the thread cavity 532. The location tube 506 may have a length ($L_T$) 538 equal to or greater than the cavity depth ($D_C$) 534. The location tube 506 may be molded plastic of a different material than the body portion 512 of the sealing connector 504a and secured to the sealing connector 504a with an adhesive or other suitable fastening means to ensure that the sealing connector 504a and the location tube 506 are operatively coupled. Also, the location tube 506 may be molded as part of the same piece as the body portion 512 of the sealing connector 504a. In an example embodiment, the inner foam pad 508 may cover both the inner wall surface 530 of the cap cavity 526 and the bottom surface 528 of the cap cavity 526. The inner foam pad 508 may have a predetermined thickness ($T_P$) 540 adapted to clean a plurality of male threads 580a, 580b, 580c, and 580d on a threaded connector port cap 108. As described herein, the plurality of male threads may be referred to generally as 580. For example, the predetermined thickness ($T_P$) 540 of the inner foam pad 508 may be thick enough to fill the space around the plurality of male threads 580 and exert an inward pressure in all directions on the plurality of male threads 580 when the inner foam pad 508 is in a compressed state. The inner foam pad 508 may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities.

In an example embodiment, the outer foam sleeve 510 may have a tubular portion 542 and a flange portion 544. The tubular portion 542 has an interior surface 546 and an exterior surface 548. The flange portion 544 has an interior surface 550 and an exterior surface 552. The exterior surface 548 of the tubular portion 542 may be adjacent to the exterior surface 552 of the flange portion 544. The interior surface 546 of the tubular portion 542 may be coupled to the location tube 506 and the interior surface 550 of the flange portion 544 may be coupled to the base surface 536 of the thread cavity 532. The outer foam sleeve 510 may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities. It should be appreciated that many of the connectors utilized in medical tubing systems, including threaded connector ports 104, trap fluid overflow within the connector ports and the threads of the connector port. The connections may often have to be cleaned to ensure that the connections meet the sanitation standards required by the user between uses. A common method for cleaning the connector ports is to flush the connector port with a cleaning solution. However, this method increases the risk of flushing the solution or debris left over from the fluid overflow back down the feeding tube. Constructing the inner foam pad 508 and/or the outer foam sleeve 510 from open-cell foam and/or luffa (loofah) sponge material advantageously traps any debris or particles cleaned from the threaded connector port 104 and/or threaded connector port cap 108 within the open-cell or fibrous matrix of the luffa (loofah) sponge and may leave the threaded connector port 104 and the threaded connector port cap 108 or second threaded connector cleaned and debris free upon removing the cleaning apparatus 502a, and advantageously eliminates the risk of flushing debris back down the feeding tube.

The exterior surface 548 of the tubular portion 542 has a predetermined diameter ($D_P$) 554 such that, upon rotating the body portion 512 radially about the longitudinal axis 518 of the sealing connector 504a, the outer foam sleeve 510 is forced outwardly into close contact with the plurality of female threads 234 of the threaded connector port 104. For example, the predetermined diameter ($D_P$) 554 of the exterior surface 548 of the tubular portion 542 may be large enough to exert pressure in all directions on the plurality of female threads 234 when the outer foam sleeve 510 is in a compressed state. The outer foam sleeve 510 is in close contact with the plurality of female threads 234 when the outer foam sleeve 510 is touching the plurality of female threads 234. Preferably, the pressure exerted by the outer foam sleeve 510 should enable the outer foam sleeve 510 to sufficiently clean (e.g., scrub) the plurality of female threads 234 in close contact with the outer foam sleeve 510. At the same time the outer foam sleeve 510 is cleaning the plurality of female threads 234 of the threaded connector port 104, the inner foam pad 508 is forced inwardly into close contact with the plurality of male threads 580 of the threaded connector port cap 108. Accordingly, the threaded connector port 104 and the threaded connector port cap 108 or a second threaded connector may advantageously be simultaneously cleaned, saving valuable clinician time.

The location tube 506 may have a textured interior surface adapted to clean an exterior surface 232 of a bore channel 230 within the threaded connector port 104. In an example embodiment, the cleaning apparatus 502a may also include an alignment peg similar to alignment peg 202. The alignment peg may be concentrically aligned with the location tube 506 and may have a length adapted to allow the clinician to align the entire length of the outer foam sleeve 510 within the threaded connector port 104. The cleaning apparatus 502a may be aligned within the threaded connector port 104 by inserting the alignment peg into the bore channel 230 of the threaded connector port 104. The alignment peg may be shorter, longer, or the same length as the location tube 506. In an example embodiment, the alignment peg may be textured or coated with an appropriate material suitable for cleaning the bore channel 230 of the threaded connector port 104. Similarly, the cleaning apparatus 502a may be aligned within the threaded connector port 104 by inserting the location tube 506 over the exterior surface 232 of the bore channel 230.

Additionally, the inner foam pad 508 of the cap cavity 526 may include a tubular foam protrusion (not pictured) aligned with the longitudinal axis 518 of the sealing connector 504a adapted to clean a cavity 582 of the threaded connector port cap 108. The tubular foam protrusion may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities. Additionally, the cap cavity 526 may include a cleaning peg (not pictured) adapted to fit tightly within the cavity 582 of the threaded connector port cap 108. The cleaning peg may be textured or coated with a suitable material adapted to clean the interior surface of the cavity 582 of the threaded connector port cap 108.

Figure 5G:
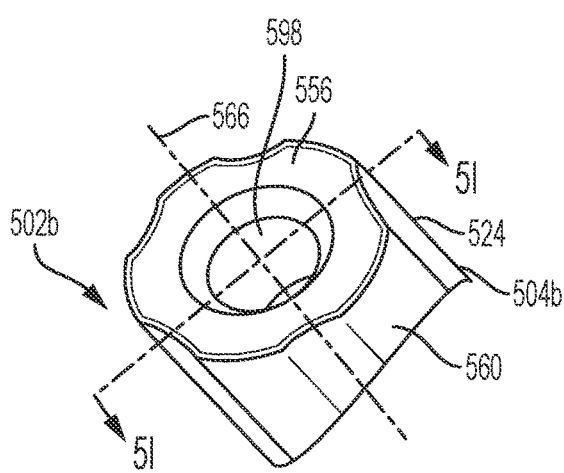
FIG. 5G is an enlarged partial view of an example cleaning apparatus, according to an example embodiment of the present disclosure.
Figure 5H:
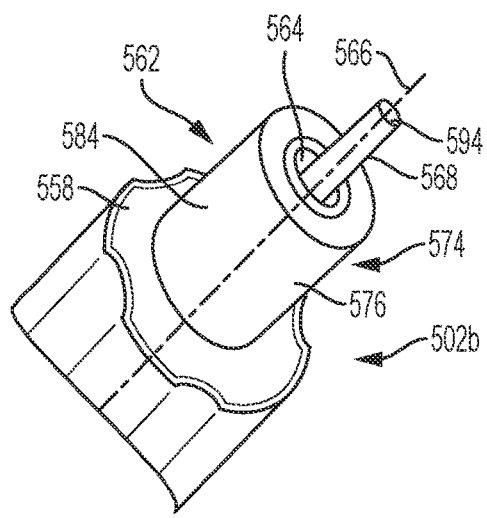
FIG. 5H is an enlarged partial view of an example cleaning apparatus, according to an example embodiment of the present disclosure.

FIGS. 5G and 5H are enlarged partial perspective views of the cleaning apparatus 502b, according to an example embodiment of the present disclosure. The cleaning apparatus 502b comprises a sealing connector 504b, an alignment peg 568, and an outer foam sleeve 574. The sealing connector 504b is shown in greater detail in FIG. 5I which depicts a cross-sectional view of the cleaning apparatus 502b, taken along line 5I-5I of FIG. 5G. The sealing connector 504b includes a body portion 524 having a first end 556 and a second end 558, an internal thread cleaning portion 562, and a longitudinal axis 566. The longitudinal axis 566 of the sealing connector 504b extends from the first end 556 of the body portion of the sealing connector 504b to the internal thread cleaning portion 562 of the sealing connector 504b. The sealing connector 504b may seal a cleaning area (e.g., area between the bore channel 230 and the female threads 436 on the threaded connector port 104) to prevent foreign material from entering the threaded connector port 104 during cleaning. For example, the internal thread cleaning portion 562 and the alignment peg 568 may seal the bore channel 230 of a threaded connector port 104 and the cleaning area. The outer foam sleeve 574 may form a seal between the cleaning area and the outside environment to prevent foreign material from entering the cleaning area during cleaning. It should be understood that the sealing connector 504b need not create an operative or hermetic seal with the threaded connector port 104. For example, the seal may act as a debris barrier.

The body portion 524 of the sealing connector 504b may include a gripping portion 560 provided between the first end 556 and the second end 558 of the sealing connector 504b. The gripping portion 560 may be textured and may include gripping members made from the same or different material than the sealing connector 504b. The gripping portion 560 need not be textured or include gripping members. Essentially, the gripping portion 560 may merely be sufficient for a clinician to grip and use the cleaning apparatus 502b (e.g., twisting action). In an example embodiment, the body portion 524 may include a cavity 598 having an inner wall surface and a base surface. The cavity 598 may provide additional gripping surfaces. Additionally, the cavity 598 may include an inner foam pad similar to inner foam pad 508 (described above), which is adapted to clean a plurality of male threads 580a, 580b, 580c, and 580d on a threaded connector port cap 108. The internal thread cleaning portion 562 of the sealing connector 504b is provided at the second end 558 of the body portion 524. In an example embodiment, the internal thread cleaning portion 562 may include a location tube 564. The location tube 564 has a length ($L_{LT2}$) 590. The location tube 564 of the cleaning apparatus 502b is aligned with the longitudinal axis 566 of the sealing connector 504b and may be coupled to the second end 558 of the sealing connector 504b. The location tube advantageously provides support for the outer foam sleeve 574 (described in more detail below). It should be appreciated that to achieve the maximum cleaning benefit from the outer foam sleeve 574, the foam sleeve should fit tightly into the female threads 436 and exert pressure in all directions on the female threads 436 when in a compressed state. For example, this may be achieved by selecting a soft foam material that compresses and fits tightly around the female threads 436 as well as a rigid backing material (e.g., location tube 564) to provide support and enable the outer foam sleeve 574 to exert pressure in all directions on the female threads 436. In another example embodiment, a more rigid outer foam sleeve 574 may be used without a location tube. For example, a more rigid outer foam sleeve 574 may serve the dual purpose of locating and cleaning.

The outer foam sleeve 574 has a tubular portion 576. The tubular portion 576 has an interior surface 578, an exterior surface 584, and a length ($L_{FS}$) 586. In an example embodiment, the length ($L_{LT2}$) 590 of the location tube 564 may be equal to the length ($L_{FS}$) 586 of the tubular portion 576. In another example embodiment, the length ($L_{LT2}$) 590 of the location tube 564 may be less than the length ($L_{FS}$) 586 of the tubular portion 576 or alternatively the length ($L_{LT2}$) 590 may be greater than the length ($L_{FS}$) 586 of the tubular portion 576. In an example embodiment, the location tube 564 may be molded plastic of a different material than the body portion 524 of the sealing connector 504b and may be secured to the sealing connector 504b with an adhesive or other suitable fastening means to ensure that the sealing connector 504b and the location tube 564 are operatively coupled. Also, the location tube 564 may be molded as part of the same piece as the body portion 524 of the sealing connector 504b. The location tube 564 may have an interior surface adapted to clean an exterior surface 232 of a bore channel 230 within the threaded connector port. For example, the location tube 564 may have inside diameter ($D_{LT}$) 594 that enables the location tube 564 to fit over and come into contact with the exterior surface 232 of the bore channel 230. In an example embodiment, the interior surface of the location tube 564 may be textured or covered with any suitable material that enables cleaning of the exterior surface 232 of the bore channel 230.

The tubular portion 576 of the outer foam sleeve 574 is adapted to engage a plurality of female threads 234 of the threaded connector port 104 along the length ($L_{FS}$) 586 of the tubular portion 576. Additionally, the exterior surface 584 of the tubular portion 576 has a predetermined diameter ($D_{TP}$) 588 such that, upon rotating the body portion 524 radially about the longitudinal axis 566 of the sealing connector 504b, the outer foam sleeve 574 is forced outwardly into close contact with the plurality of female threads 234 of the threaded connector port 104. For example, the predetermined diameter ($D_{TP}$) 588 of the exterior surface 584 of the tubular portion 576 may be large enough to exert pressure in all directions on the plurality of female threads 234 when the outer foam sleeve 574 is in a compressed state. The outer foam sleeve 574 is in close contact with the plurality of female threads 234 when the outer foam sleeve 574 is touching the plurality of female threads 234. Preferably, the pressure exerted by the outer foam sleeve 574 should enable the outer foam sleeve 574 to sufficiently clean (e.g., scrub) the plurality of female threads 234 in close contact with the outer foam sleeve 574.

In an example embodiment, the body portion 524 of the sealing connector 504b may include a cavity 598. Additionally, the cavity 598 may include an inner foam pad similar to inner foam pad 508 (described above), such that at the same time the outer foam sleeve 574 is cleaning the plurality of female threads 234 of the threaded connector port 104, the inner foam pad is forced inwardly into close contact with the plurality of male threads 580 of the threaded connector port cap 108. Accordingly, the threaded connector port 104 and the threaded connector port cap 108 or a second threaded connector may advantageously be simultaneously cleaned, saving valuable clinician time.

The outer foam sleeve 574 may be made of several different materials, including, polyether foam, polyester foam, ethafoam, volara, open-cell foam, closed-cell sponge rubber, open-cell sponge rubber, cellulose, scrubber foams, sponges, luffa (loofah) sponge material, and the like, or any other suitable material to provide a suitable level of flexibility, rigidity, and absorbent qualities. It should be appreciated that many of the connectors utilized in medical tubing systems, including threaded connector ports 104, trap fluid overflow within the connector ports and the threads of the connector port. The connections may often have to be cleaned to ensure that the connections meet the sanitation standards required by the user between uses. A common method for cleaning the connector ports 104 is to flush the connector port 104 with a cleaning solution. However, this method increases the risk of flushing the solution or debris left over from the fluid overflow back down the feeding tube 106. Constructing the outer foam sleeve 574 and/or inner foam pad from open-cell foam and/or sponge material advantageously traps any debris or particles cleaned from the threaded connector port 104 and/or threaded connector port cap 108 within the open-cell or fibrous matrix of the sponge and may leave the threaded connector port 104 and the threaded connector port cap 108 or second threaded connector cleaned and debris free upon removing the cleaning apparatus 502b, and advantageously eliminates the risk of flushing debris back down the feeding tube. In an example embodiment, the outer foam sleeve 574 may include a flange portion, similar to flange portion 544 described above.

The alignment peg 568 is aligned with the longitudinal axis 566 of the sealing connector 504b and coupled to the second end 558 of the body portion 524. The alignment peg 568 may be molded plastic of a different material than the body portion 524 and may be secured to the body portion 524 with an adhesive or other suitable fastening means to ensure that the body portion 524 and the alignment peg 568 are operatively coupled. Also, the alignment peg 568 may be molded as part of the same piece as the body portion 524. The alignment peg 568 has an outside diameter ($D_{AP}$) 570 and a length ($L_{AP}$) 572. The length ($L_{AP}$) 572 of the alignment peg 568 may extend beyond the location tube 564 and the outer foam sleeve 574 to allow the clinician to easily align the entire length of the outer foam sleeve 574 within the threaded connector port 104. It should be appreciated that it may be more difficult for a clinician to articulate the placement of the cleaning apparatus 502b within the threaded connector port 104 if the alignment peg 568 is considerably shorter than the length of the outer foam sleeve 574, however, in an example embodiment, the length ($L_{AP}$) 572 of the alignment peg 568 may be shorter than the length ($L_{FS}$) 586 of the tubular portion 576 of the outer foam sleeve 574.

The cleaning apparatus 502b may be aligned within the threaded connector port 104 by inserting the alignment peg 568 into the bore channel 230 of the threaded connector port 104. For example, a clinician may insert the distal end 594 of the alignment peg 568 into the bore channel 230. In an example embodiment, the alignment peg 568 may be textured or coated with an appropriate material suitable for cleaning the bore channel 230 of the threaded connector port 104. It should be appreciated that it may be more difficult for a clinician to articulate the placement of the cleaning apparatus 502b within the threaded connector port 104 if the outside diameter ($D_{AP}$) 570 of the alignment peg 568 at the distal end 594 is about the same as the inside diameter of the bore channel 230. In an example embodiment, the alignment peg 568 may be cylindrical with a rounded end, which advantageously allows a clinician to insert the alignment peg 568 into the bore channel 230 with ease. In another example embodiment, the alignment peg 568 may be tapered such that the outside diameter ($D_{AP}$) 570 decreases along the length ($L_{AP}$) 572 towards the distal end 594, which advantageously allows a clinician to easily align the cleaning apparatus 502b with the threaded connector port 104. Similarly, the cleaning apparatus 502b may be aligned within the threaded connector port 104 by inserting the location tube 564 over the exterior surface 232 of the bore channel 230. For example, the alignment peg 568 and the location tube 564 may both assist a clinician with aligning the cleaning apparatus 502b with the threaded connector port 104.

Figure 5I:
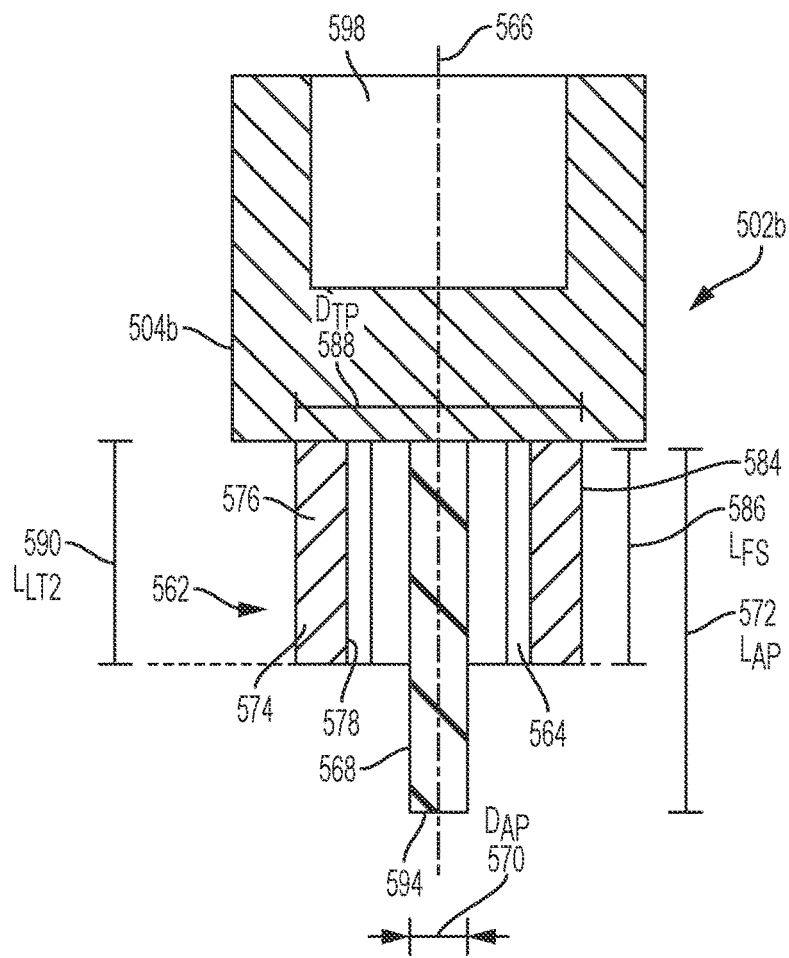
FIG. 5I is a cross-sectional view of an example cleaning apparatus, according to an example embodiment of the present disclosure.
Figure 5J:
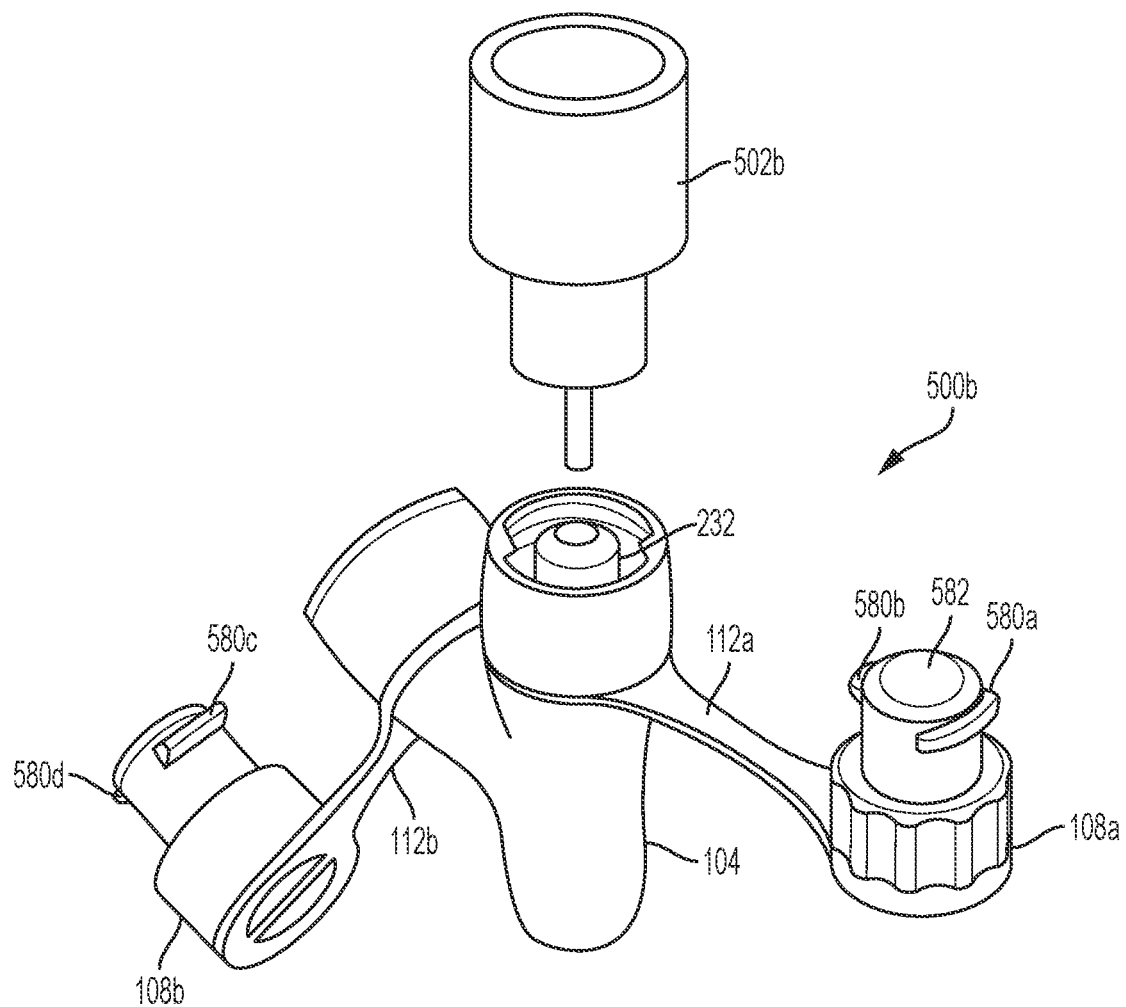
FIG. 5J is a perspective view of an example cleaning system, according to an example embodiment of the present disclosure.
Figure 5K:
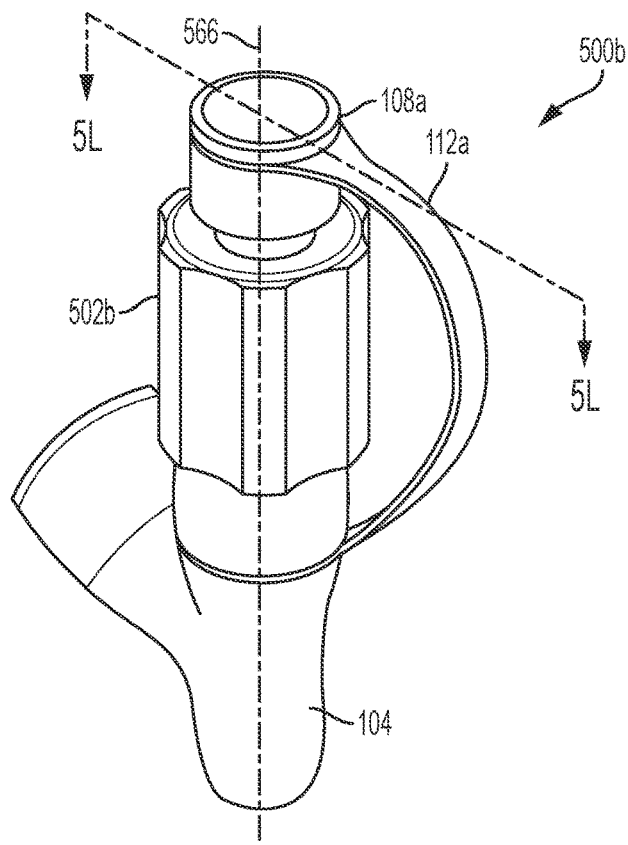
FIG. 5K is a perspective view of an example cleaning system, according to an example embodiment of the present disclosure.
Figure 5L:
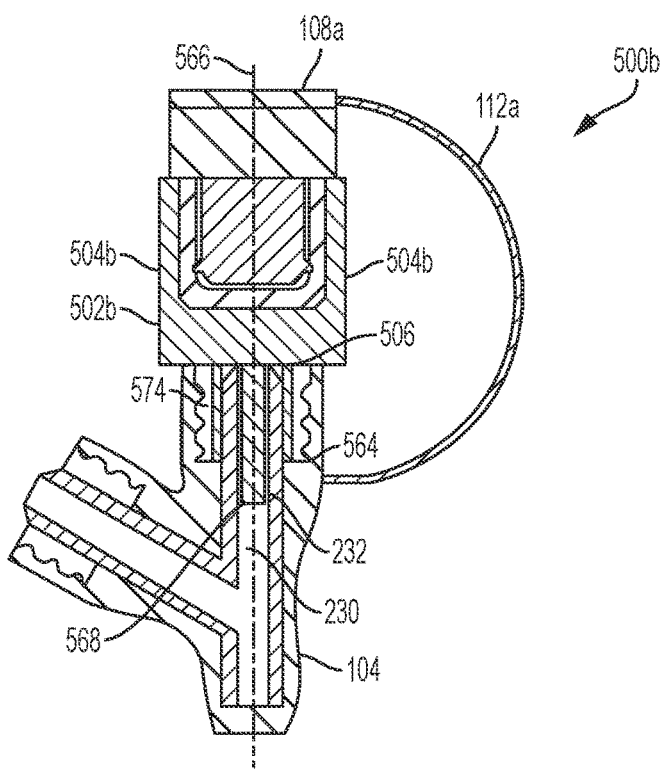
FIG. 5L is a cross-sectional view of an example cleaning system, according to an example embodiment of the present disclosure.

FIGS. 5J and 5K are perspective views of an example cleaning system 500b, according to an example embodiment of the present disclosure. A cross-sectional view of the cleaning system 500b is illustrated in FIG. 5L, taken along line 5L-5L of FIG. 5K. The cleaning system 500b includes a cleaning apparatus 502b and a threaded connector port 104. The cleaning apparatus 502b is described in FIG. 5G, FIG. 5H, and FIG. 5I. The location tube 564 of the cleaning apparatus 502b is aligned with the longitudinal axis 566 of the sealing connector 504b.

Figure 5M:
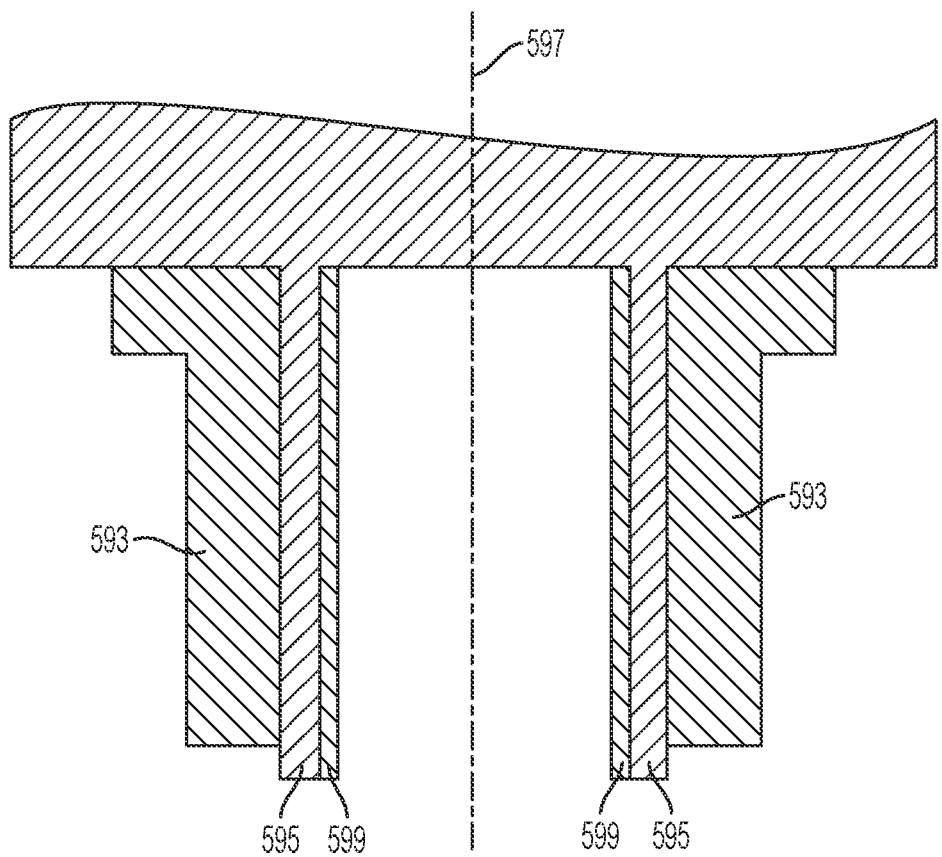
FIG. 5M is an enlarged partial cross-sectional view of an example cleaning apparatus, according to an example embodiment of the present disclosure.

FIG. 5M is an enlarged partial cross-sectional view of an example cleaning apparatus (e.g., cleaning apparatus 502a, 502b) taken along a line similar to 5C-5C of FIG. 5A or 5I-5I of FIG. 5G. In an example embodiment, the cleaning apparatus (e.g., cleaning apparatus 502a, 502b) may include a location tube 595, an outer foam sleeve 593, and a longitudinal axis 597. In an example embodiment, the location tube 595 may be textured or covered with any suitable material that enables cleaning of the exterior surface 232 of the bore channel 230. In an example embodiment, an interior surface of the location tube 595 may be covered with a sealing material 599. For example, the sealing material 599 may be a hollow cylinder of compressible material that is coupled to the interior surface of the location tube 595. It should be appreciated that threaded connector ports 104 may have bore channels 230 of various shapes and sizes. In an example embodiment, the sealing material 599 may be adapted to form a seal between the exterior surface 232 of the bore channel 230 and the location tube 595. For example, the sealing material 599 may have an appropriate thickness and compressibility to form a seal around various different sizes of bore channels 230.

Figure 6A:
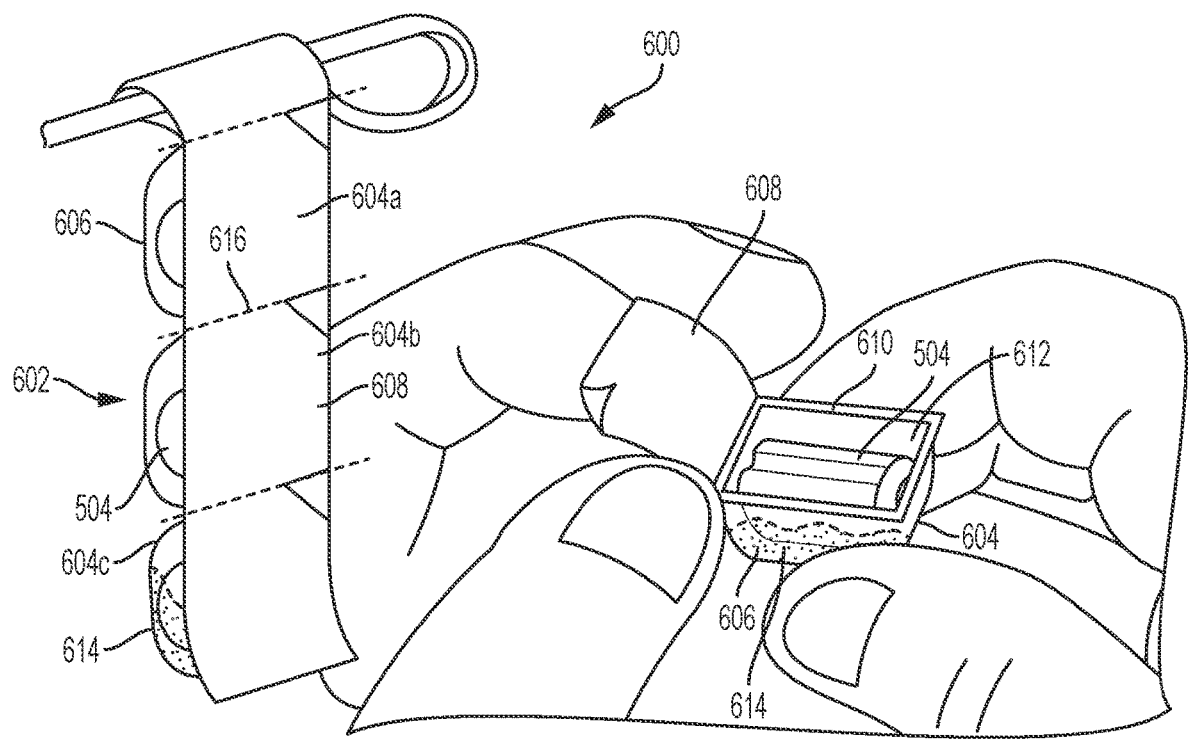
FIG. 6A is a perspective view of an example cleaning assembly, according to an example embodiment of the present disclosure.

FIG. 6A is a perspective view of a cleaning assembly 600. The cleaning assembly 600 comprises a strip of disposable containers 602. Each disposable container 604a, 604b, and 604c includes a basin 606, a removable closure lid 608, and a sealing connector 504. Hereinafter, each disposable container 604a, 604b, and 604c may generally be referred to as 604. Each disposable container 604 of the strip of disposable containers 602 is separated by perforated edges 616. The basin 606 has a cavity 610 with an opening 612. Each cavity 610 is at least partially filled with a wetting fluid 614. In an example embodiment of the present disclosure, the wetting fluid 614 may be an antimicrobial fluid (e.g., alcohol such as isopropyl alcohol), a saline solution, or any other suitable fluid. In an example embodiment, each cavity 610 may be entirely filed with wetting fluid 614. The removable closure lid 608 is attached to the basin 606 and adapted to cover the opening 612 of the cavity 610. The sealing connector 504 (e.g., 504a, 504b) included in each disposable container 604a, 604b, and 604c is described in FIGS. 5A through 5L.

Figure 6B:
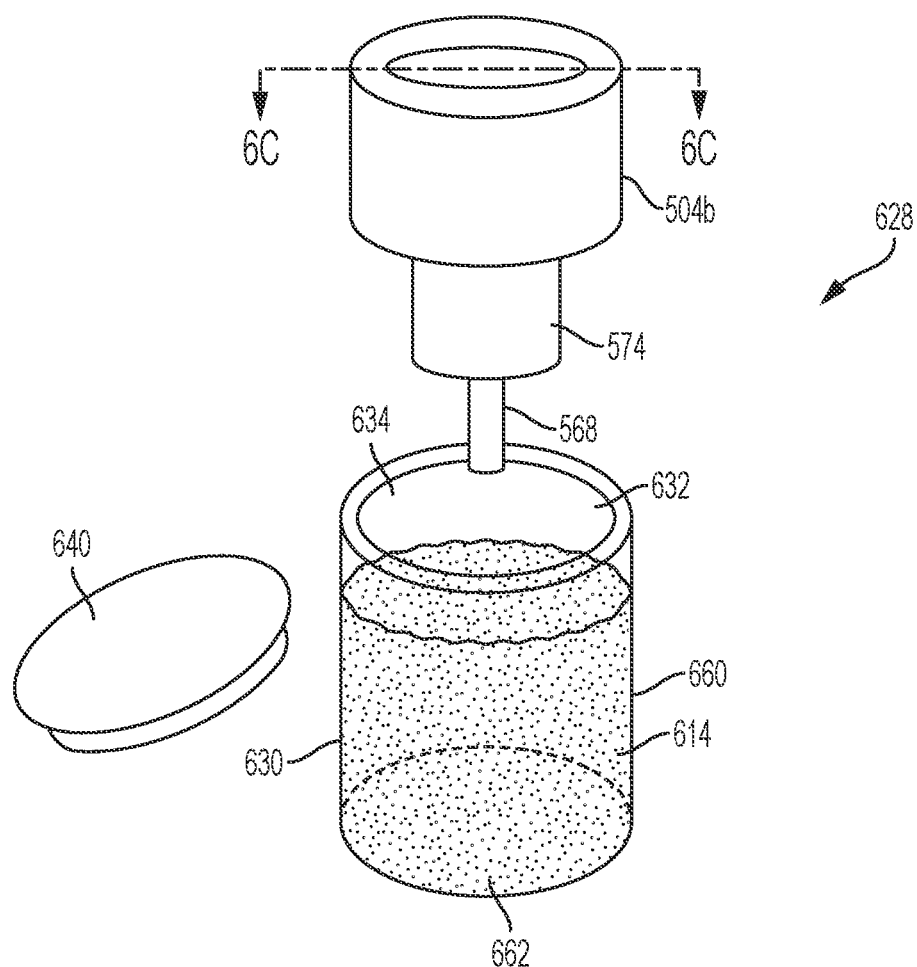
FIG. 6B is perspective view of an example cleaning assembly, according to an example embodiment of the present disclosure.

FIG. 6B is a perspective view of a cleaning assembly 628. The cleaning assembly 628 comprises a basin 630 and a sealing connector 504b. The basin 630 has a side wall 660 and base 662. For example, side wall 660 may be a single cylindrical side wall, or may be structured as multiple side walls for other geometries (e.g., square, triangular, rectangular, elliptical, etc.). The side wall 660 forms a cavity 632 with an opening 634. The cavity 632 of the basin 630 is at least partially filled with a wetting fluid 614. The wetting fluid 614 may be an antimicrobial fluid (e.g., alcohol such as isopropyl alcohol), a saline solution, or any other suitable fluid. The cavity 632 has a cavity depth 636 and a cavity diameter 638. It should be appreciated that several different geometrical configures for that cavity may be used, and the cavity need not be cylindrical. The cavity depth 636 may be greater than or equal to the largest of the length ($L_{AP}$) 572 of the alignment peg 568, the length ($L_{FS}$) 586 of the tubular portion 576 of the outer foam sleeve 574, and the length ($L_{LT2}$) 590 of the location tube 564. Additionally, the cavity diameter 638 is greater than the external diameter ($D_{TP}$) 588 of the outer foam sleeve 574. The cavity depth 636 and cavity diameter 638 are sized such that the entire internal thread cleaning portion 562 and outer foam sleeve 574 can fit within the cavity 632, thereby enabling the wetting fluid 614 to wet and sanitize the cleaning surfaces (e.g., outer foam sleeve 574, location tube 564, and/or alignment peg 568) of the cleaning apparatus 502b. In an example embodiment, the alignment peg 568 and/or the location tube 564 may touch the bottom of the basin 630 to provide additional stability to the cleaning assembly 628.

In another example embodiment, the cleaning assembly 628 may include a removable closure lid 640. The removable closure lid 640 may be attached to the basin 630 via a threaded connection, a press fit connection (e.g., the closure lid 640 may include a gasket or a channel that accepts the basin), a peel away connection, or the like. In an example embodiment, the cleaning apparatus 502b may fit entirely within the basin 630 and may be secured within the basin 630 by the removable closure lid 640. For example, the basin 630 and the removable closure lid 640 of the cleaning assembly 628 may house the cleaning apparatus 502b. The cleaning assembly 628 may be packaged for pre-wetted applications or dry applications. For example, in a pre-wetted application, the cavity 632 of the basin 630 may be pre-filled with wetting fluid 614. In a dry application, the cleaning assembly 628 may be packaged without any wetting fluid 614 in the cavity 632 of the basin 630. In the dry application, the user may remove the removable closure lid 640 and add a wetting fluid 614 to the cavity 632 of the basin 630. For example, in the dry application discussed above, the user may select the wetting fluid 614 (e.g., isopropyl alcohol, saline, etc.) that is preferred for the cleaning/wetting application.

Figure 6C:
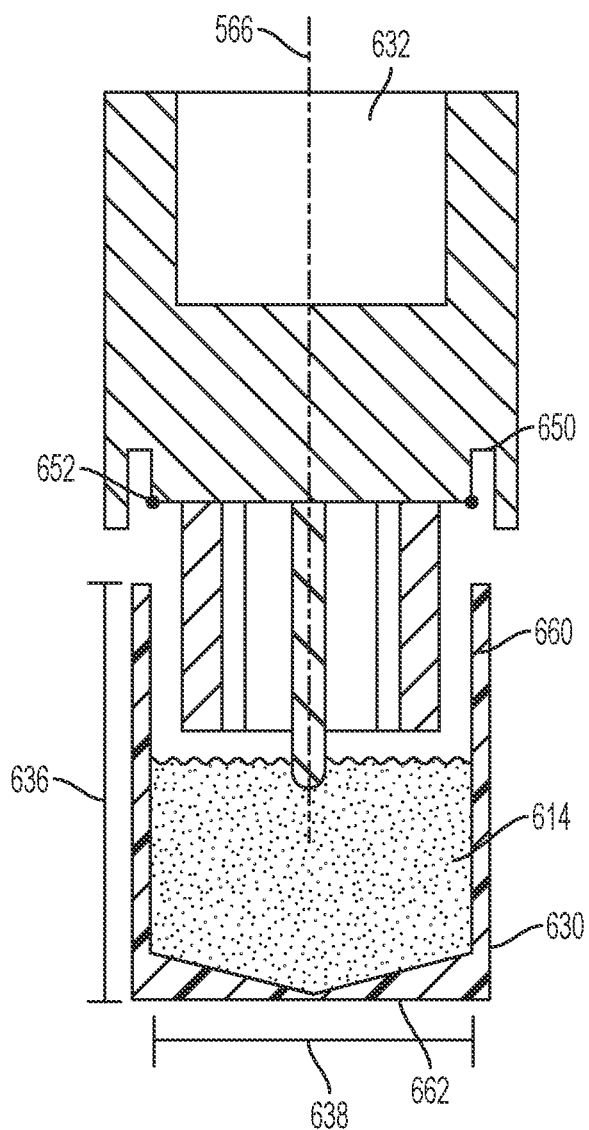
FIG. 6C is a cross-sectional view of an example cleaning assembly, according to an example embodiment of the present disclosure.
Figure 6D:
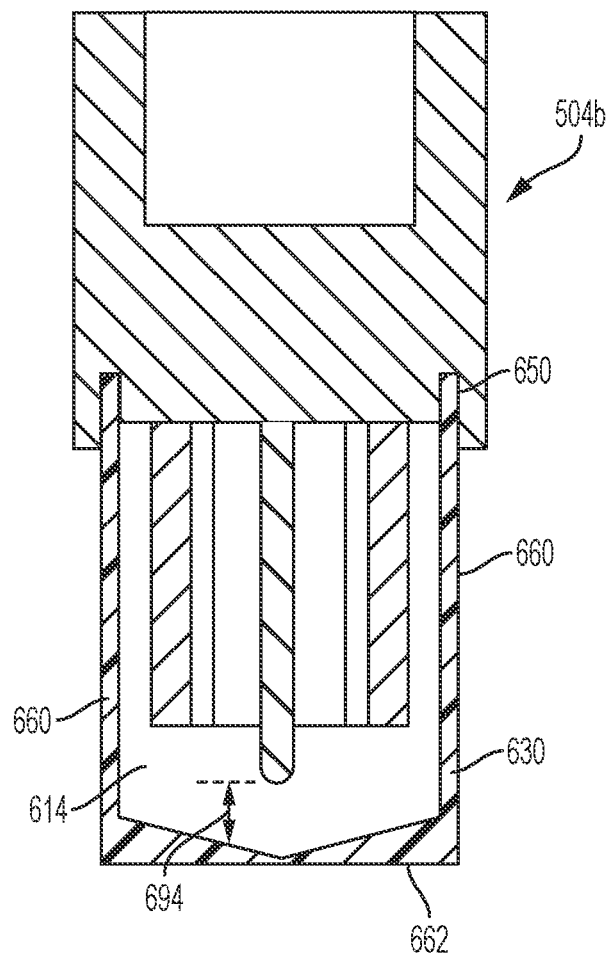
FIG. 6D is a cross-sectional view of an example cleaning assembly, according to an example embodiment of the present disclosure.

FIGS. 6C and 6D are cross-sectional views of the cleaning assembly 628, taken along line 6C-6C of FIG. 6B. As illustrated in FIG. 6C, the sealing connector 504b may include a channel 650 on the second end 558 of the body portion 524. The channel 650 may be adapted to receive the side wall 660 of the basin 630. For example, the channel 650 may match the geometry (e.g., shape and thickness) of the side wall 660 to form a press fit connection between the sealing connector 504b and the basin 630. In another example embodiment, the sealing connector 504b may include a gasket 652, such as an o-ring, on the second end 558 of the body portion 524 that is adapted to form a seal between the sealing connector 504b and the basin 630. In yet another example embodiment, the sealing connector 504b may include threads that are configured to engage threads included on the basin 630 to enable a clinician to screw the sealing connector 504b onto the basin 630. It should be appreciated that other features may be implemented on the sealing connector 504b and/or basin 630 enabling the sealing connector 504b to form a seal with the basin 630. For example, in another example embodiment, the gasket 652 may reside on the outside surface of the sealing connector 504b such that the gasket 652 forms a seal with the inside of the side wall 660 of the basin 630. Additionally, the sealing connector 504b may include threads on the outside surface of the sealing connector 504b that are configured to engage threads included on the inside of the side wall 660 of the basin 630.

In an example embodiment, the cleaning assembly 628 may include the cleaning apparatus 502b pre-coupled to the basin 630. For example, the sealing connector 504b may serve as a cap for the basin 630 to form a seal such that the cleaning surfaces (e.g., outer foam sleeve 574, location tube 564, and/or alignment peg 568) of the cleaning apparatus 502b are in contact with the wetting fluid 614. Upon removing the cleaning apparatus 502b from the basin 630 (e.g., unscrewing, pulling apart, etc.), the outer foam sleeve 574 will be pre-wetted and ready to use for a first cleaning. Pre-coupling the cleaning apparatus 502b to the basin 630 advantageously provides a cleaning apparatus 502b with a pre-wet outer foam sleeve 574 and sanitized cleaning surfaces, thereby eliminating the need for the clinician to perform additional steps to wet and sanitize the cleaning apparatus 502b. Depending on the amount of wetting fluid 614 in the basin, the clinician may shake the cleaning assembly 628 (e.g., cleaning apparatus 502b pre-coupled to the basin 630) to ensure that outer foam sleeve 574 is sufficiently wetted with the wetting fluid 614. For example, in a pre-wetted application, the cavity 632 of the basin 630 may be pre-filled with wetting fluid 614 (e.g., with the basin 630 approximately half-way full). In a dry application, the cleaning assembly 628 may be packaged without any wetting fluid 614 in the cavity 632 of the basin 630. In the dry application, the user may remove the sealing connector 502b and add a wetting fluid 614 to the cavity 632 of the basin 630. For example, in the dry application discussed above, the user may select the wetting fluid 614 (e.g., isopropyl alcohol, saline, etc.) that is preferred for the cleaning/wetting application.

In the example with the removable closure lid 640, a clinician may seal the basin 630 with the sealing connector 504b after removing the removable closure lid 640. For example, the clinician may place the sealing connector over the opening 634 and may press and/or screw the sealing connector 504b onto the basin 630. As the clinician moves the sealing connector 504b over the opening of the basin 630 and towards the base 662 of the basin 630, the cleaning surfaces (e.g., outer foam sleeve 574, location tube 564, and/or alignment peg 568) of the cleaning apparatus 502b come into contact with the wetting fluid 614. Once the sealing connector 504b and the basin 630 form a seal, the clinician may shake the coupled sealing connector 504b and/or the basin 630 to further wet and/or sanitize the cleaning surfaces of the cleaning apparatus 502b. In an example embodiment, the cavity depth 636 and a cavity diameter 638 may enable suitable clearance between the cleaning surfaces, the side wall 660, and the base 662 of the basin 630 to allow any of the unwanted particulate matter to settle at the bottom of the basin 630 such that the unwanted particulate matter is no longer in contact with the cleaning apparatus 502b. For example, the cavity depth 636 may be configured to provide a clearance 694 between a distal end 594 of the alignment peg 568 and the base 662 of the basin 630 to allow unwanted material to settle at the bottom of the basin 630 without contacting the alignment peg 568. After the cleaning apparatus 502b is sufficiently wet and/or sanitized, the clinician may remove the cleaning apparatus 502b from the basin 630. In another example embodiment, the alignment peg 568 and/or the location tube 564 may touch the bottom of the basin 630 to provide additional stability to the cleaning assembly 628.

Figure 7A:
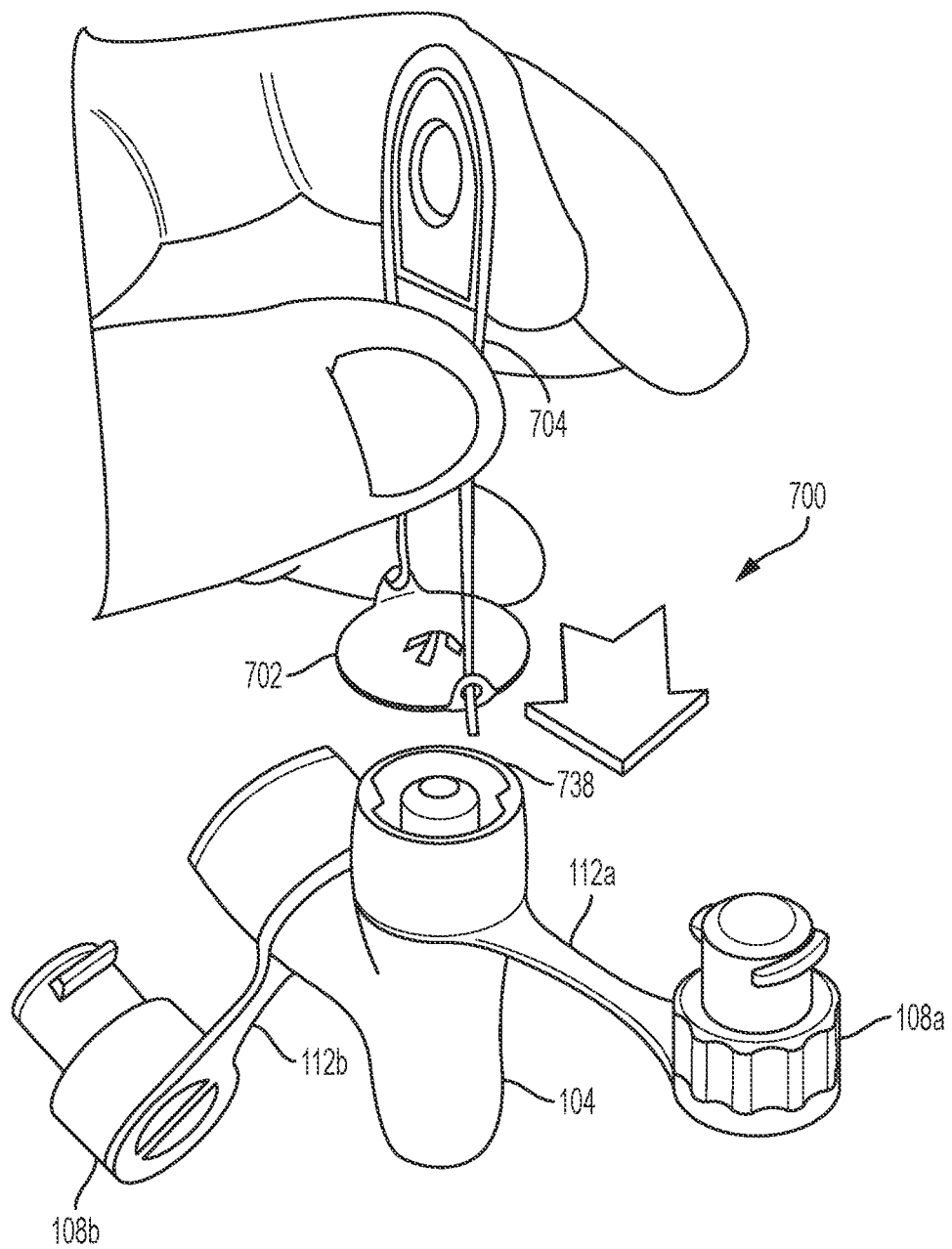
FIG. 7A is a perspective view of an example sealing system, according to an example embodiment of the present disclosure.
Figure 7B:
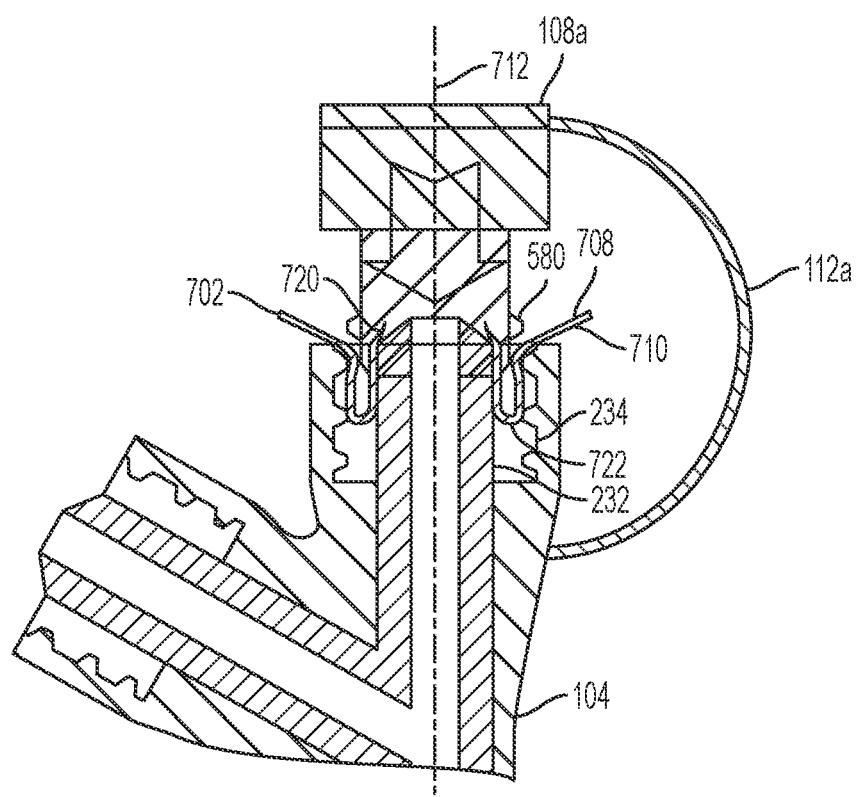
FIG. 7B is a cross-sectional view of an example disposable liner and threaded port connector of a sealing system, according to an example embodiment of the present disclosure.
Figure 7C:
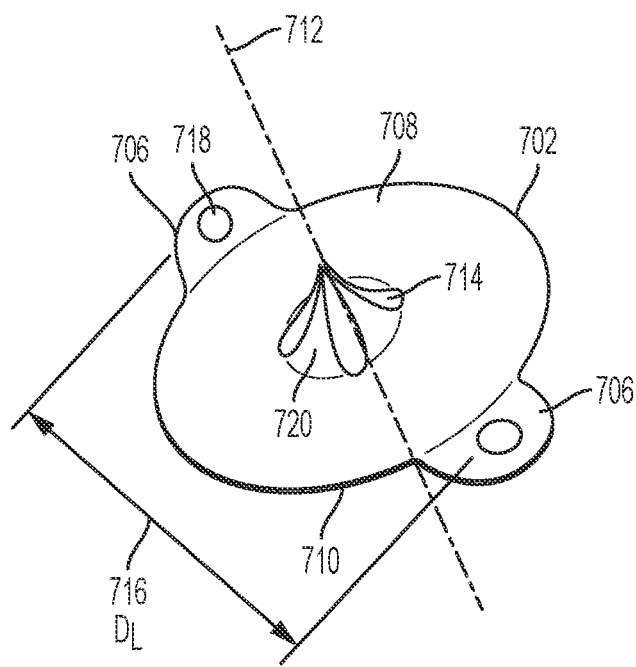
FIG. 7C is a perspective view of an example disposable liner, according to an example embodiment of the present disclosure.
Figure 7D:
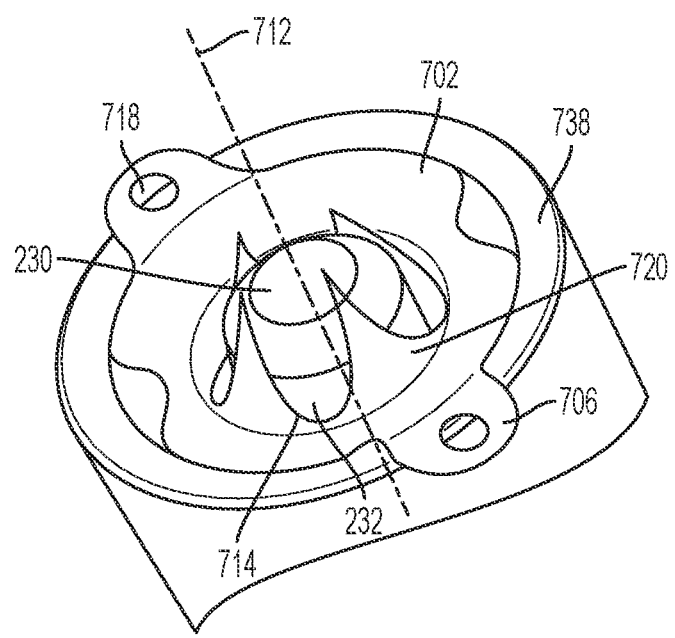
FIG. 7D is a perspective view of an example disposable liner placed within a threaded connector port, according to an example embodiment of the present disclosure.

FIG. 7A is a perspective view of a sealing system 700 and FIG. 7B is a cross-sectional view of disposable liner 702 and a threaded connector port 104, according to an example embodiment of the present disclosure. The sealing system 700 includes a disposable liner 702, a placement tool 704, and a threaded connector port 104. A perspective view of the disposable liner 702 is shown in FIG. 7C and FIG. 7D, according to an example embodiment of the present disclosure. The disposable liner 702 includes two locator flaps 706, a top side 708, a bottom side 710, a longitudinal axis 712, a liner opening 714, and a diameter ($D_L$) 716. The longitudinal axis 712 extends from the top side 708 of the disposable liner 702 to the bottom side 710 of the disposable liner 702. The liner opening 714 is axially aligned with the longitudinal axis 712 of the disposable liner 702. The diameter ($D_L$) 716 of the disposable liner 702 is equal to the distance between the two locator flaps 706. In an example embodiment, the disposable liner 702 may be oval, square, rectangular, oblong, elliptical, diamond/rhombus shaped, or any other suitable shape. For example, the diameter ($D_L$) 716 of the disposable liner 702 may apply to any shape used for the disposable liner 702. Each of the two locator flaps 706 includes an aperture 718. The liner opening 714 includes a plurality of tails 720 that are adapted to engage an exterior surface 232 of a bore channel 230 within the threaded connector port 104. The diameter ($D_L$) 716 of the disposable liner 702 is adapted to engage a plurality of female threads 234 within the threaded connector port 104 and the exterior surface 232 of the bore channel 230 within the threaded connector port 104, such that upon the insertion and rotation of a threaded connector port cap 108 or a second threaded connector (not pictured) radially about the longitudinal axis 712 of the disposable liner 702, the bottom side 710 of the disposable liner 702 is forced outwardly into close contact with the plurality of female threads 234 of the threaded connector port 104 and the exterior surface 232 of the bore channel 230, and the top side 708 of the disposable liner 702 is forced inwardly into close contact with a plurality of male threads 580 of the threaded connector port cap 108 or a second threaded connector (not pictured) such that the disposable liner 702 creates a seal 722 between the threaded connector port 104 and the threaded connector port cap 108 or between the threaded connector port 104 and a second threaded connector (not pictured). The disposable liner 702 may be made of several different materials that provide a suitable level of flexibility, compressibility, strength, and absorbent qualities. For example, the disposable liner 702 may have the flexibility and strength to advantageously allow a clinician to apply the disposable liner 702 to a threaded connector port 104, screw on the threaded connector port cap 108, then unscrew the threaded connector port cap 108 and screw in a second threaded connector while the liner stays in place.

Figure 7E:
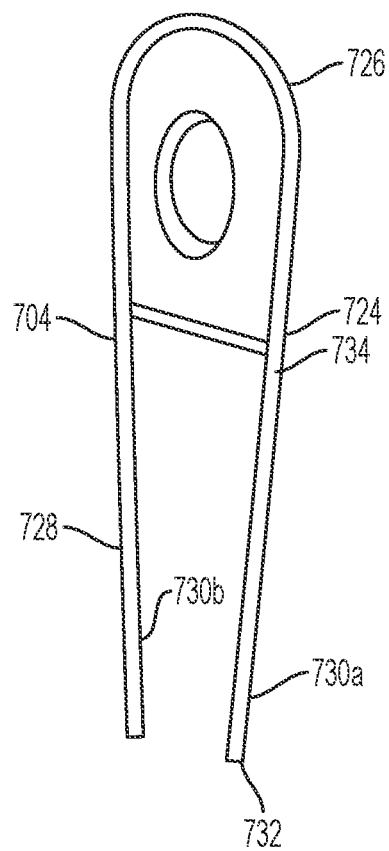
FIG. 7E is a perspective view of an example placement tool, according to an example embodiment of the present disclosure.
Figure 7F:
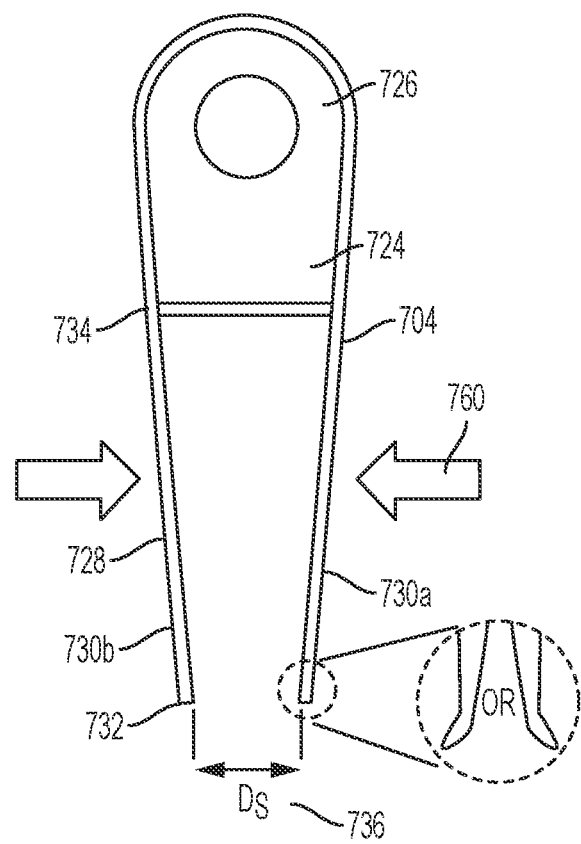
FIG. 7F is a side view of an example placement tool, according to an example embodiment of the present disclosure.

A perspective view of the placement tool 704 is shown in FIG. 7E, and a side view of the placement tool 704 is shown in FIG. 7F, according to an example embodiment of the present disclosure. The placement tool 704 includes a handle body 724, a first end 726, a second end 728, and two locator fingers 730a and 730b. As described herein, the two locator fingers 730a and 730b may be referred to generally as 730. The two locator fingers 730 each have a respective distal end 732 and a proximal end 734. The distal end 732 is distally located from the handle body 724, and the proximal end 734 is proximally located at the handle body 724. In an example embodiment, the two locator fingers 730 may be straight and parallel to each other, or the two locator fingers 730 may bend in towards each other or away from each other when the placement tool 704 is in a relaxed state. Additionally, the distal ends 732 of the two locator fingers 730 may be straight, may bend inwards, or may bend outwards depending on the structure of the disposable liner 702. For example, the locator fingers 730 having distal ends 732 that bend outwards advantageously reduce the risk of prematurely releasing the disposable liner 702, and the locator fingers 730 having distal ends 732 that bend inwards advantageously allow for easier release of the disposable liner 702. The placement tool 704 may be constructed from a variety of metals and/or plastics that provide a suitable level of flexibility and rigidity. For example, the placement tool 704 may include a flexible material which includes a construction of one or more materials including stainless steel, polyethylene, silicon, thermoplastic, and the like, and may also be latex-free. The two locator fingers 730 have a separation distance ($D_S$) 736 at the respective distal ends 732. The separation distance ($D_S$) 736 is greater than the diameter ($D_L$) 716 of the disposable liner 702. For example, in a relaxed state, the separation distance ($D_S$) 736 of the two locator fingers on the placement tool 704 is larger than the diameter ($D_L$) of the disposable liner 702. The two locator fingers 730 are axially aligned with the respective locator flaps 706 of the disposable liner 702. The two locator fingers 730 are adapted to engage the respective apertures 718 of the two locator flaps 706 in response to an inward pressure 760 applied between the respective distal ends 732 and proximal ends 734 of the two locator fingers 730 to decrease the separation distance ($D_S$) 736 of the locator fingers 730 and allow positioning of the locator fingers 730 within the apertures 718 of the two locator flaps 706. The two locator fingers 730 hold the disposable liner 702 in tension in response to decreasing the application of the inward pressure 760. It should be appreciated that only a nominal force may be required to generate the inward pressure 760 necessary to decrease the separation distance ($D_S$) 736 to within the clearance of the apertures 718 of the two locator flaps 706 on the disposable liner 702. The placement tool 704 is adapted to release the disposable liner 702 by positioning the disposable liner 702 over a top surface 738 of the threaded connector port 104, aligning the liner opening 714 and the bore channel 230 along the longitudinal axis 712 of the disposable liner 702, and applying the inward pressure 760 between the respective distal ends 732 and proximal ends 734 of the two locator fingers 730 to decrease the separation distance ($D_S$) 736 of the two locator fingers 730 and allow the two locator fingers 730 to withdraw from the apertures 718 of the two locator flaps 706. Proper placement of the disposable liner 702 is important because poor placement may prevent a seal 722 from forming between the threaded connector port 104 and the threaded connector port cap 108 or between two threaded connectors. In an example embodiment, the placement tool 704 may include three or more locator fingers, and the disposable liner 702 may include three or more corresponding locator flaps. In an alternative embodiment, the placement tool 704 may be adapted to receive an outward pressure or pressing force by the clinician to decrease the separation distance ($D_S$) 736 of the two locator fingers 730.

Figure 8:
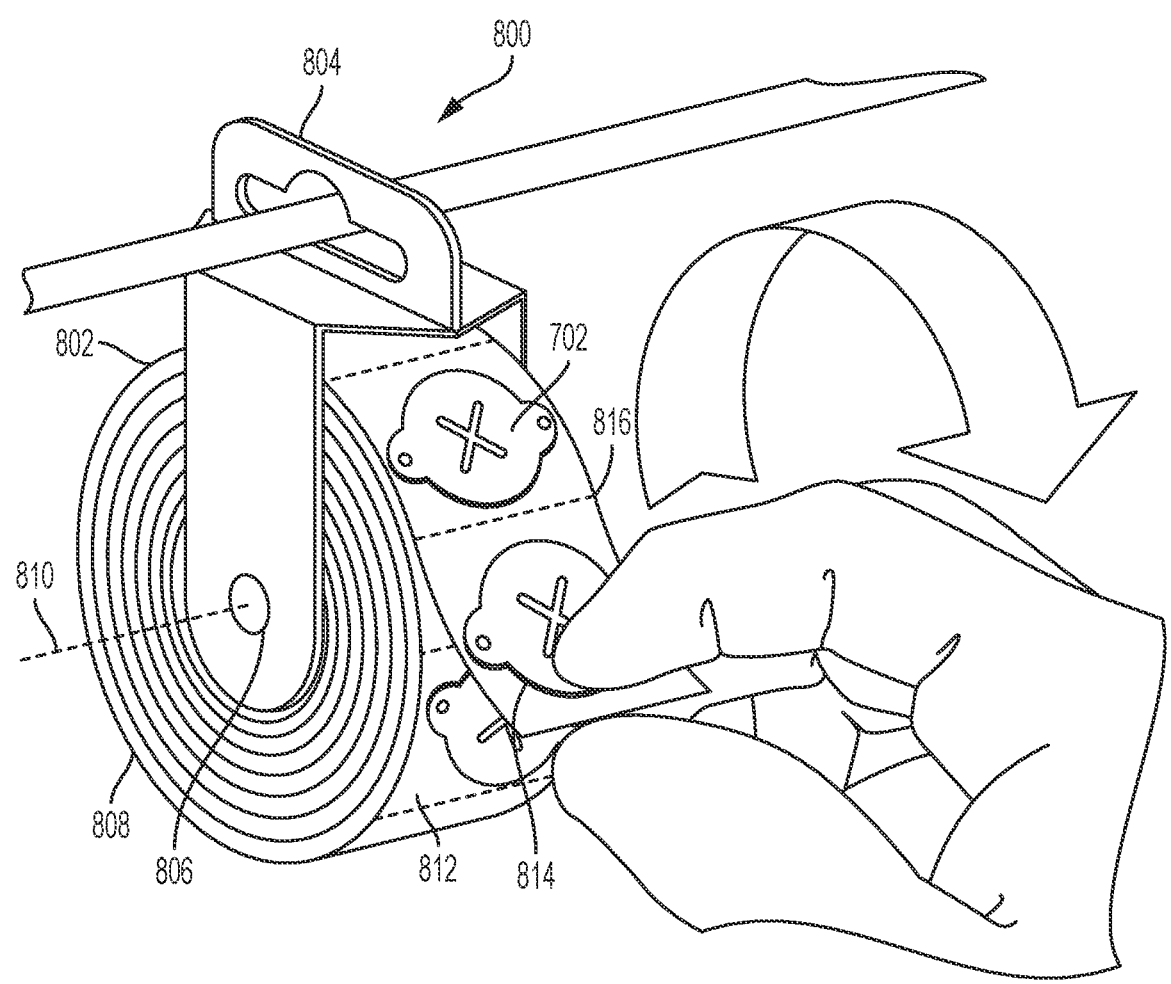
FIG. 8 is a perspective view of an example sealing assembly, according to an example embodiment of the present disclosure.

FIG. 8 is a perspective view of a sealing assembly 800, according to an example embodiment of the present disclosure. The assembly includes a disposable liner dispenser 802 and a placement tool 704. The disposable liner dispenser 802 includes a frame 804, a roller bar 806, and a liner reel 808. The roller bar 806 defines a second longitudinal axis 810 for receiving the liner reel 808. The liner reel 808 includes a plurality of disposable liners 812 attached to a leading disposable liner 814 to be dispensed. The plurality of disposable liners 812 are separated by perforated edges 816. Each disposable liner 702 of the plurality of disposable liners 812 is as described in FIG. 7B, FIG. 7C, and FIG. 7D.

Figure 9A:
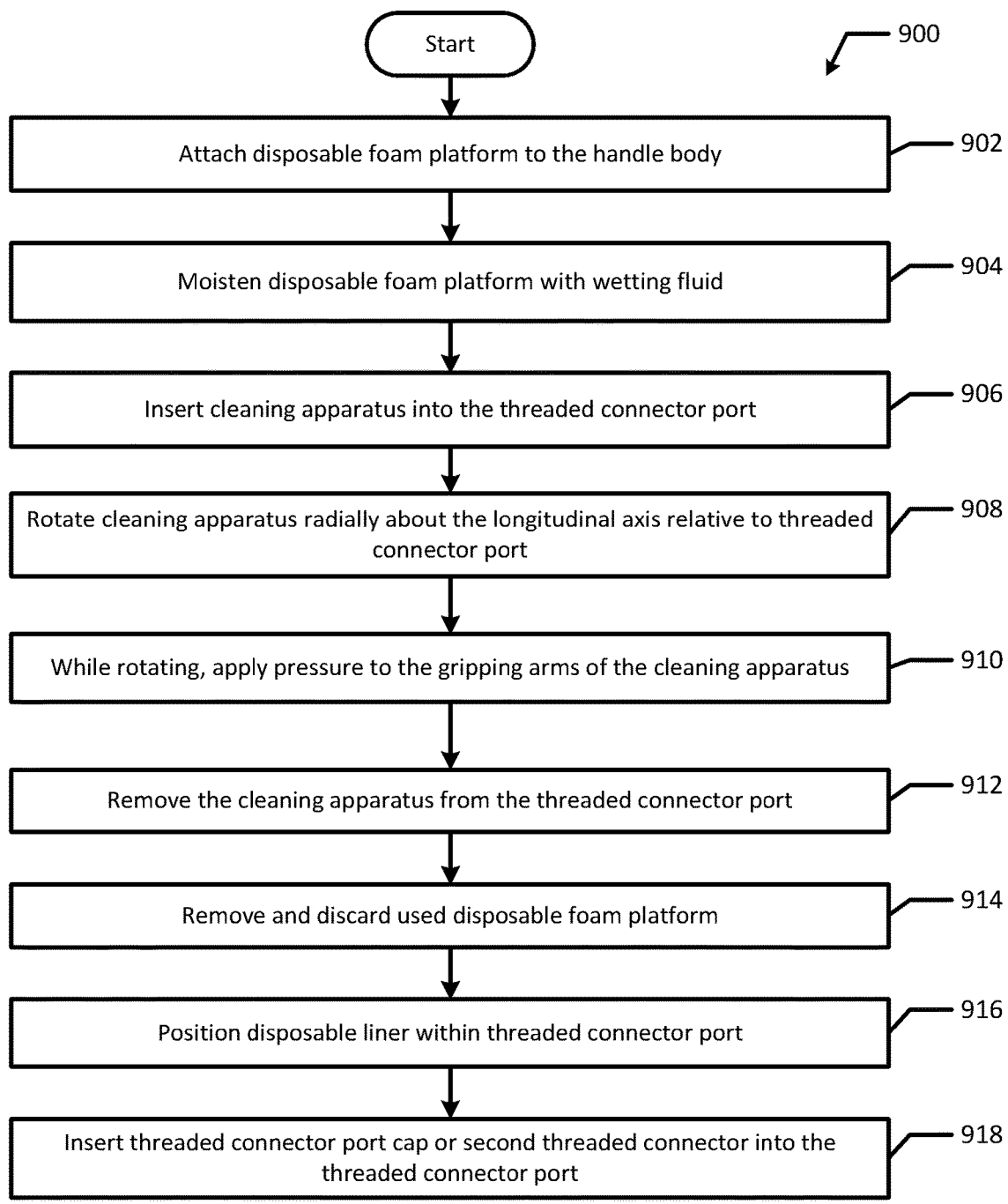
FIG. 9A includes a flowchart illustrating an example process for cleaning a threaded connector port, according to an example embodiment of the present disclosure.

FIG. 9A includes a flowchart of an example process 900 for cleaning a threaded connector port 104. Although process 900 is described with reference to the flowchart illustrated in FIG. 9A, it will be appreciated that many other methods of performing the acts associated with the process 900 may be used. For example, the order of many of the blocks may be changed, many blocks may be intermittently repeated or continually performed, certain blocks may be combined with other blacks, and many of the blocks described are optional or may only be contingently performed.

The example process 900 may begin with a clinician attaching a disposable foam platform 218 to the handle body 200 of a cleaning apparatus 102 (block 902). Then, if the disposable foam platform 218 is not already moistened, the clinician may moisten the disposable foam platform 218 with a wetting fluid 614 (block 904). In an example embodiment of the present disclosure, the wetting fluid 614 may be an antimicrobial fluid (e.g., alcohol such as isopropyl alcohol), a saline solution, or any other suitable fluid. Then, the clinician may insert the cleaning apparatus 102 into the threaded connector port 104 (block 906). When inserting the cleaning apparatus 102, the clinician may utilize the alignment peg 202 to ensure that the disposable foam platform 218 is properly engaging the plurality of female threads 234 and the exterior surface 232 of the bore channel 230. Then, the clinician may rotate the cleaning apparatus 102 about the longitudinal axis 260 relative to the threaded connector port 104 (block 908). While rotating, the clinician may apply pressure 270 to the pair of gripping arms 208 of the cleaning apparatus 102 such that the pair of cleaning arms 210 force the disposable foam platform 218 into close contact with the plurality of female threads 234 and the exterior surface 232 of the bore channel 230 (block 910). The clinician may repeat the steps of blocks 908 and 910 until the threaded connector port 104 is sufficiently cleaned, and then, the clinician may remove the cleaning apparatus 102 from the threaded connector port 104 (block 912). Then the clinician may remove and discard the used disposable foam platform 218 (block 914). For example, the clinician may use his hands to remove the disposable foam platform 218 with the assistance of the scallops 236 molded into the handle body 200. Also, the clinician may use a tool to pry the disposable foam platform 218 from the handle body 200. The clinician may position a disposable liner 702 within the threaded connector port 104 (block 916) described in greater detail below. Then, the clinician may inserted a threaded connector port cap 108 or a second threaded connector into the threaded connector port 104 (block 916).

Figure 9B:
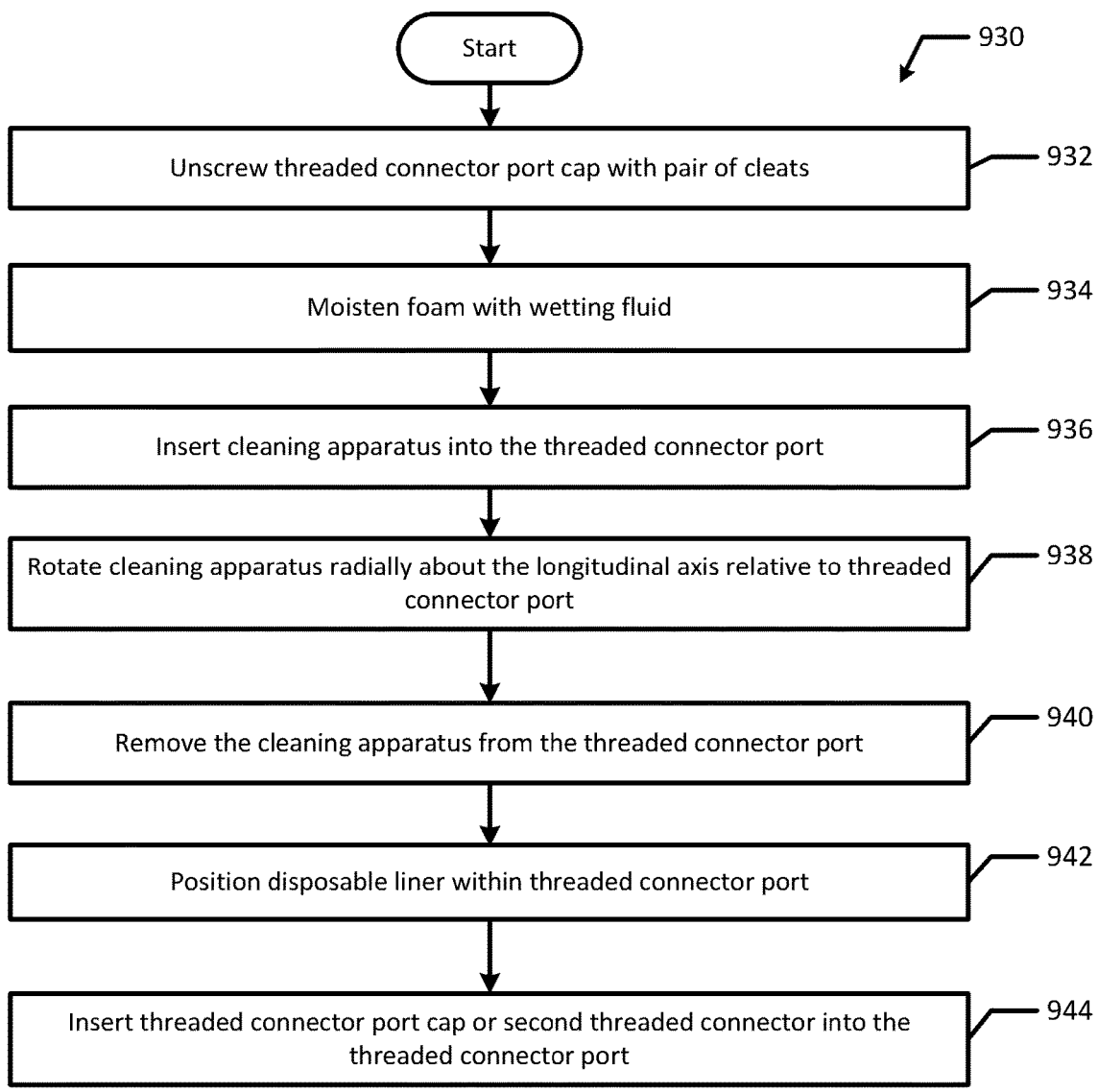
FIG. 9B includes a flowchart illustrating an example process for cleaning a threaded connector port, according to an example embodiment of the present disclosure.

FIG. 9B includes a flowchart of an example process 930 for cleaning a threaded connector port 104. Although process 930 is described with reference to the flowchart illustrated in FIG. 9B, it will be appreciated that many other methods of performing the acts associated with the process 930 may be used. For example, the order of many of the blocks may be changed, many blocks may be intermittently repeated or continually performed, certain blocks may be combined with other blacks, and many of the blocks described are optional or may only be contingently performed.

The example process 930 may begin with a clinician unscrewing a threaded connector port cap 108 with the pair of cleats 438 included on the handle body 402 of the cleaning apparatus 401 (block 932). Then, the clinician may moisten the foam with wetting fluid (block 934). The foam may be a disposable foam platform 218, a first plurality of foam pads 404, and/or a second plurality of foam pads 430. In an example embodiment of the present disclosure, the wetting fluid 614 may be an alcohol such as isopropyl alcohol, and the like, or any other suitable fluid such as a saline solution. Then, the clinician may insert the cleaning apparatus (102, 401) into the threaded connector port 104 (block 936). When inserting the cleaning apparatus (102, 401) the clinician may utilize an alignment peg 202, a location tube 506, or the like to ensure that the disposable foam platform 218 or plurality of foam pads (404, 430) is properly engaging the plurality of female threads 234 and the exterior surface 232 of the bore channel 230. Then, the clinician may rotate the cleaning apparatus (102, 401) radially about the longitudinal axis (260, 480) relative to the threaded connector port 104 (block 938). Then, the clinician may remove the cleaning apparatus (102, 401) from the threaded connector port 104 (block 940). The clinician may position a disposable liner 702 within the threaded connector port 104 (block 942) described in greater detail below. Then, the clinician may inserted a threaded connector port cap 108 or a second threaded connector into the threaded connector port 104 (block 944).

Figure 9C:
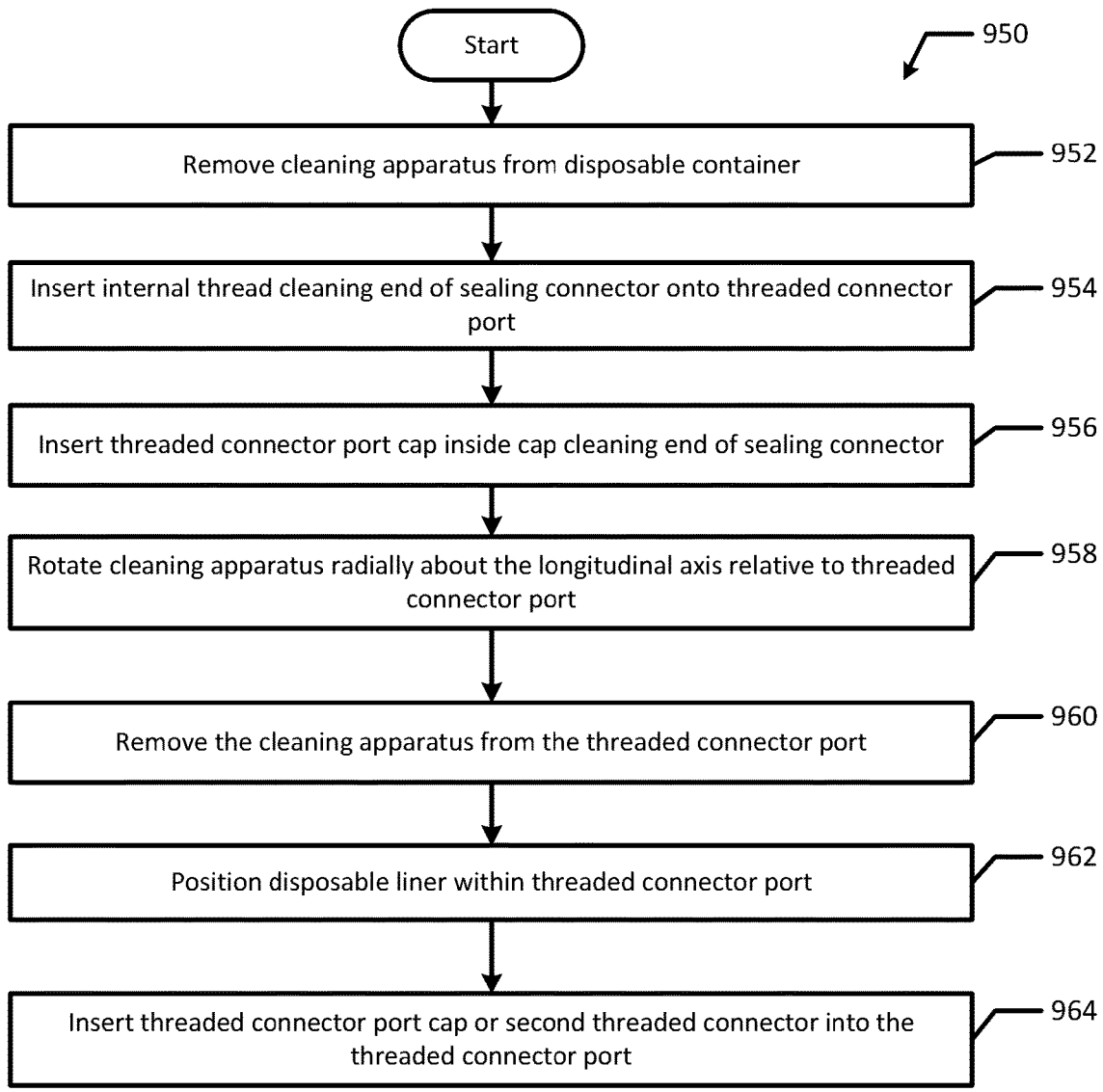
FIG. 9C includes a flowchart illustrating an example process for cleaning a threaded connector port, according to an example embodiment of the present disclosure.

FIG. 9C includes a flowchart of an example process 950 for cleaning a threaded connector port 104. Although process 930 is described with reference to the flowchart illustrated in FIG. 9C, it will be appreciated that many other methods of performing the acts associated with the process 950 may be used. For example, the order of many of the blocks may be changed, many blocks may be intermittently repeated or continually performed, certain blocks may be combined with other blacks, and many of the blocks described are optional or may only be contingently performed.

The example process 950 may begin with a clinician removing a cleaning apparatus 502 from a disposable container 604 (block 952). This may require the clinician to remove a disposable container 604 from the strip of disposable containers 602. The clinician may open the disposable container 604 by removing the removable closure lid 608 and the cleaning apparatus 502 inside. It should be appreciated that the cleaning apparatus 502 is pre-moistened with wetting fluid 614 which may be included in the disposable container 604. The clinician may still be wearing gloves to avoid contamination of the cleaning apparatus 502, but the gloves may not be necessary based on the type of wetting fluid 614 used. For example, the cleaning apparatus 502 may advantageously be moistened with a wetting fluid 614, such as a strong antimicrobial fluid, that would prevent any cross contamination caused from directly handling the cleaning apparatus 502, advantageously allowing a clinician to quickly handle the cleaning apparatus 502, saving valuable clinician time. Then, the clinician may insert the internal thread cleaning end 516 of the sealing connector 504 onto the threaded connector port 104 (block 954). The clinician may align the cleaning apparatus 502 onto the threaded connector port 104 by using the location tube 506 to position the cleaning apparatus 502 over the bore channel 230 and thereby centering the cleaning apparatus 502 onto the threaded connector port 104. Then the clinician may insert the threaded connector port cap 108 inside the cap cleaning end 514 of the sealing connector 504 (block 956). It should be appreciated that the cap cleaning end 514 may be used for other threaded connectors that include a plurality of male threads 580. Then, the clinician may rotate the cleaning apparatus 502 radially about the longitudinal axis 518 (block 958) such that the inner foam pad 508, outer foam sleeve 510, and the location tube 506 respectively clean the plurality of male threads 580 on the threaded connector port cap 108, the plurality of female threads 234 in the threaded connector port 104, and the exterior surface 232 of the bore channel 230. The clinician may repeat the step of (block 958) until the threaded connector port 104 is sufficiently cleaned. Then, the clinician may remove the cleaning apparatus 502 by removing the threaded connector port cap 108 or other threaded connector and pulling the cleaning apparatus 502 from the threaded connector port 104 (block 960). The clinician may position a disposable liner 702 within the threaded connector port 104 (block 962) described in greater detail below. Then, the clinician may inserted a threaded connector port cap 108 or a second threaded connector into the threaded connector port 104 (block 964).

Figure 9D:
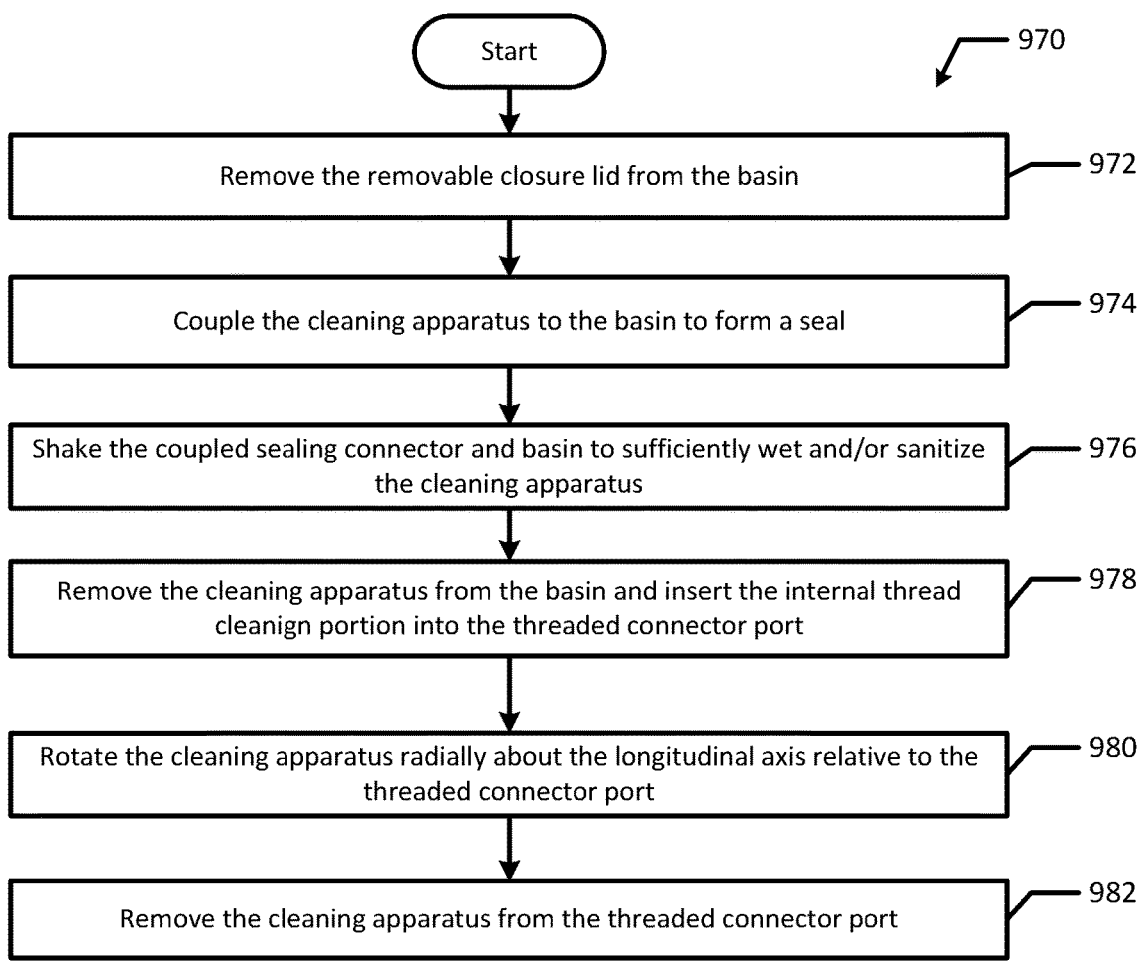
FIG. 9D includes a flowchart illustrating an example process for cleaning a threaded connector port, according to an example embodiment of the present disclosure.

FIG. 9D includes a flowchart of an example process 970 for cleaning a threaded connector port 104. Although process 970 is described with reference to the flowchart illustrated in FIG. 9D, it will be appreciated that many other methods of performing the acts associated with the process 970 may be used. For example, the order of many of the blocks may be changed, many blocks may be intermittently repeated or continually performed, certain blocks may be combined with other blacks, and many of the blocks described are optional or may only be contingently performed.

The example process 970 may begin with a clinician removing the removable closure lid 640 from the basin 630 (block 972). For example, the clinician may pull off, peel away, or unscrew the removable closure lid 640. Then, the clinician may couple the cleaning apparatus 502b to the basin 630 to form a seal (block 974). In an example embodiment, the clinician may press-fit the sealing connector 504b onto the side wall 660 of the basin 630. In another example embodiment, the clinician may screw the sealing connector 504b onto the basin 630. Then, the clinician may shake the coupled sealing connector 504b and basin 630 to sufficiently wet and/or sanitize the cleaning apparatus 502b (block 976). Then, the clinician may remove cleaning apparatus 502b from the basin and insert the internal thread cleaning portion 562 of the sealing connector 504b into the threaded connector port 104 (block 978). The clinician may align the cleaning apparatus 502b onto the threaded connector port 104 by using the alignment peg 568 to position the cleaning apparatus 502b over the bore channel 230 and thereby centering the cleaning apparatus 502b onto the threaded connector port 104. In an example embodiment, the clinician may also align the cleaning apparatus 502*b* onto the threaded connector port 104 by using the location tube 564. Then, the clinician may rotate the cleaning apparatus 502*b* radially about the longitudinal axis 566 (block 980) such that the outer foam sleeve 574 and the location tube 564 respectively clean the plurality of male threads 580 on the threaded connector port cap 108 and the exterior surface 232 of the bore channel 230. Additionally, the alignment peg 568 may also clean the clean the bore channel 230 of the threaded connector port 104. The clinician may repeat the step of (block 980) until the threaded connector port 104 is sufficiently cleaned. Then, the clinician may remove the cleaning apparatus 502*b* from the threaded connector port 104 (block 982). The clinician may repeat the step of (blocks 974 through 980) to perform additional cleaning of the threaded connector port 104.

Figure 9E:
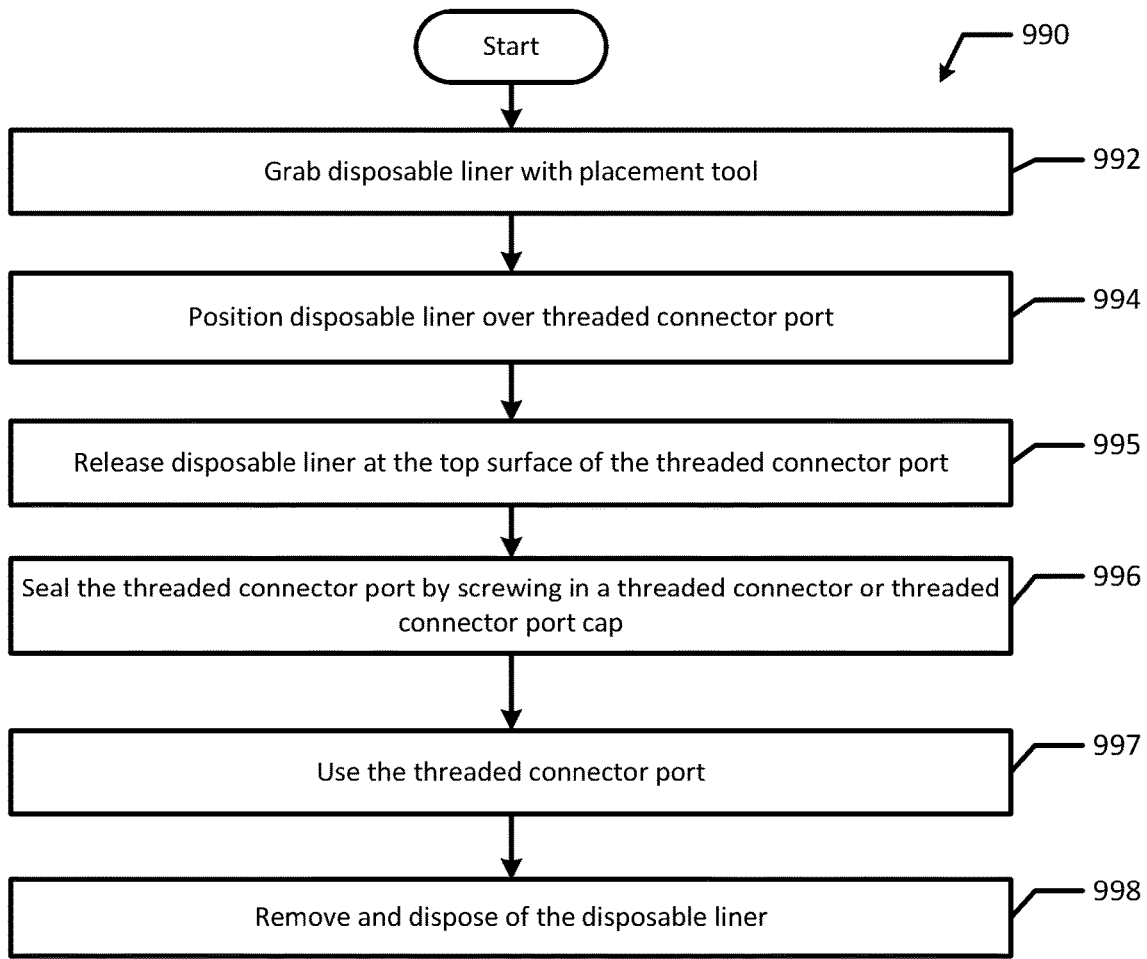
FIG. 9E includes a flowchart illustrating an example process for sealing a threaded connector port, according to an example embodiment of the present disclosure.

FIG. 9E includes a flowchart of an example process 990 for sealing a threaded connector port 104. Although process 990 is described with reference to the flowchart illustrated in FIG. 9E, it will be appreciated that many other methods of performing the acts associated with the process 990 may be used. For example, the order of many of the blocks may be changed, many blocks may be intermittently repeated or continually performed, certain blocks may be combined with other blacks, and many of the blocks described are optional or may only be contingently performed.

The example process 990 may begin with a clinician grabbing a disposable liner 702 with the placement tool 704 (block 992). This may require the clinician to remove a leading disposable liner 814 from the liner reel 808 including a plurality of disposable liners 812. Also, the clinician may remove the leading disposable liner 814 by tearing the perforated edges 816, and the clinician may additionally be required to remove a top plastic layer on the packaging that is designed to protect the liners. In order to grab the disposable liner 702 with the placement tool 704, the clinician may axially align the two locator fingers 730 of the placement tool 704 with the apertures 718 of the locator flaps 706 on the disposable liner 702. Once aligned, the clinician may apply an inward pressure 760 between the distal ends 732 and proximal ends 734 of the two locator fingers 730 to decrease the separation distance ($D_S$) 736 of the two locator fingers 730 until the separation distance ($D_S$) 736 is within the allowable tolerance to enable the two locator fingers 730 to be inserted into the apertures 718. Then, the clinician may decrease the inward pressure 760 thereby allowing the placement tool 704 to hold the disposable liner 702 in tension. Next, the clinician may position the disposable liner 702 over the threaded connector port 104 (block 994). The clinician may position the disposable liner 702 over a top surface 738 of the threaded connector port 104 and align the liner opening 714 and the bore channel 230 along the longitudinal axis 712 of the disposable liner 702. Then, the clinician may release the disposable liner 702 at the top surface 738 of the threaded connector port 104 (block 995). To release the disposable liner 702, the clinician may apply the inward pressure 760 between the respective distal ends 732 and proximal ends 734 of the two locator fingers 730 to decrease the separation distance ($D_S$) 736 of the locator fingers 730 and allow the two locator fingers 730 to withdraw from the apertures 718 of the two locator flaps 706. Then, the clinician may seal the threaded connector port 104 by screwing in a second threaded connector or a threaded connector port cap 108 (block 996). The clinician may press the liner into place with his hands if they are properly sanitized or with a pair of medical gloves. It should be appreciated that proper placement of the disposable liner 702 is important because poor placement may prevent a seal 722 from forming between the threaded connector port 104 and the threaded connector port cap 108 or between two threaded connectors. The seal 722 may be achieved by inserting and screwing in the threaded connector port cap 108 or another threaded connector into the threaded connector port 104. For example, the disposable liner 702 may move, stretch, and compress as need without tearing when the threaded connector port cap 108 or a second threaded connector is screwed into the threaded connector port 104. Then, the clinician may use the threaded connector port 104 (block 997). Then, the clinician may remove and dispose of the disposable liner 702 (block 998). Accordingly, the use of the disposable liner 702 advantageously creates a seal 722 between the threaded connector port 104 and a second threaded connector or a threaded connector port cap 108 and keeps the associated surfaces and threads (e.g., plurality of female threads 234 and exterior surface 232 of bore channel 230) clean such that no further cleaning may be required upon removal of the disposable liner 702.

The cleaning apparatus 102, cleaning apparatus 401, cleaning apparatus 502*a* and 502*b,* and sealing system 700 may all be used in conjunction with each other. The clinician may choose to use certain apparatus or systems depending on the level of cleaning needed and type of application the medical tubing is being used for. While some embodiments may provide for quicker cleaning, others may do a more thorough job.

It should be understood that various changes and modifications to the example embodiments described herein will be apparent to those skilled in the art. Such changes and modifications can be made without departing from the spirit and scope of the present subject matter and without diminishing its intended advantages. It is therefore intended that such changes and modifications be covered by the appended claims. Also, it should be appreciated that the features of the dependent claims may be embodied in the systems, methods, and apparatus of each of the independent claims.

The invention is claimed as follows:

1. A cleaning apparatus for use in connection with a threaded connector port for a feeding tube, the apparatus comprising:
    a handle body having a longitudinal axis extending from a first end of the handle body to a second end of the handle body, wherein the handle body includes a grip portion extending upwards from the first end of the handle body and a pair of cleaning arms extending downwards from the second end of the handle body; and
    a disposable foam platform coupled to the second end of the handle body, wherein
    the grip portion comprises a pair of gripping arms,
    the pair of cleaning arms are pivotally connected to the gripping arms by a pivot pin enclosed within the handle body, and the pair of cleaning arms are urged apart by applying a pressure at the pair of gripping arms in an inward direction towards the longitudinal axis of the handle body such that the pressure is transferred through the pivot pin to urge the pair of cleaning arms apart,
    the disposable foam platform includes a tubular hollow portion aligned with the longitudinal axis of the handle body,
    the disposable foam platform has an attachment end and a cleaning end, the attachment end of the disposable foam platform is coupled to the second end of the handle body, the attachment end of the disposable foam platform includes at least one cavity for receiving at least one of the pair of cleaning arms, and the cleaning end of the disposable foam platform is adapted to clean a plurality of female threads of the threaded connector port and an exterior surface of a bore channel within the threaded connector port when the handle body is rotated radially about the longitudinal axis relative to the threaded connector port.

2. A cleaning apparatus for use in connection with a threaded connector port for a feeding tube, the apparatus comprising:

a handle body having a longitudinal axis extending from a first end of the handle body to a second end of the handle body, wherein the handle body includes a grip portion extending upwards from the first end of the handle body and a pair of cleaning arms extending downwards from the second end of the handle body;

a disposable foam platform coupled to the second end of the handle body; and an alignment peg aligned with the longitudinal axis of the handle body and coupled to the second end of the handle body, the alignment peg having an outside diameter smaller than an internal diameter of a bore channel of the threaded connector port and having a length extending beyond the pair of cleaning arms, wherein the alignment peg is configured to be inserted into the bore channel of the threaded connector port; wherein the disposable foam platform includes a tubular hollow portion aligned with the longitudinal axis of the handle body, the disposable foam platform has an attachment end and a cleaning end, the attachment end of the disposable foam platform is coupled to the second end of the handle body, the attachment end of the disposable foam platform includes at least one cavity for receiving at least one of the pair of cleaning arms, and the cleaning end of the disposable foam platform is adapted to clean a plurality of female threads of the threaded connector port and an exterior surface of the bore channel within the threaded connector port when the handle body is rotated radially about the longitudinal axis relative to the threaded connector port.

3. A cleaning apparatus for use in connection with a threaded connector port for a feeding tube, the apparatus comprising:

a handle body having a longitudinal axis extending from a first end of the handle body to a second end of the handle body, wherein the handle body includes a grip portion extending upwards from the first end of the handle body and at least two pairs of cleaning arms extending downwards from the second end of the handle body; and a disposable foam platform coupled to the second end of the handle body, wherein the disposable foam platform includes a tubular hollow portion aligned with the longitudinal axis of the handle body, the disposable foam platform has an attachment end and a cleaning end, the attachment end of the disposable foam platform is coupled to the second end of the handle body, the attachment end of the disposable foam platform includes at least one cavity for receiving at least one pair of cleaning arms, and the cleaning end of the disposable foam platform is adapted to clean a plurality of female threads of the threaded connector port and an exterior surface of a bore channel within the threaded connector port when the handle body is rotated radially about the longitudinal axis relative to the threaded connector port.

4. A cleaning apparatus for use in connection with a threaded connector port for a feeding tube, the apparatus comprising:

a handle body having a longitudinal axis extending from a first end of the handle body to a second end of the handle body, wherein the handle body includes a grip portion extending upwards from the first end of the handle body and a pair of cleaning arms extending downwards from the second end of the handle body; and a disposable foam platform coupled to the second end of the handle body, wherein the disposable foam platform includes a tubular hollow portion aligned with the longitudinal axis of the handle body, the disposable foam platform has an attachment end and a cleaning end, the attachment end of the disposable foam platform is coupled to the second end of the handle body, the attachment end of the disposable foam platform includes at least two pairs of cavities for receiving the cleaning arms, and the cleaning end of the disposable foam platform is adapted to clean a plurality of female threads of the threaded connector port and an exterior surface of a bore channel within the threaded connector port when the handle body is rotated radially about the longitudinal axis relative to the threaded connector port.

5. A cleaning apparatus for use in connection with a threaded connector port for a feeding tube, the apparatus comprising:

a handle body having a longitudinal axis extending from a first end of the handle body to a second end of the handle body, wherein the handle body includes a grip portion extending upwards from the first end of the handle body and a pair of cleaning arms extending downwards from the second end of the handle body; and a disposable foam platform coupled to the second end of the handle body, wherein the handle body includes at least two scallops adapted to assist in the removal of the disposable foam platform, the disposable foam platform includes a tubular hollow portion aligned with the longitudinal axis of the handle body, the disposable foam platform has an attachment end and a cleaning end, the attachment end of the disposable foam platform is coupled to the second end of the handle body, the attachment end of the disposable foam platform includes at least one cavity for receiving at least one of the pair of cleaning arms, and the cleaning end of the disposable foam platform is adapted to clean a plurality of female threads of the threaded connector port and an exterior surface of a bore channel within the threaded connector port when the handle body is rotated radially about the longitudinal axis relative to the threaded connector port.

6. A cleaning system for use in connection with enteral feeding, the system comprising:
- a foam platform dispenser housing having a front side and a back side, wherein
  - the front side has a plurality of attachment end openings and the back side has a plurality of cleaning end openings,
  - the plurality of attachment end openings are axially aligned with the plurality of cleaning end openings, and
  - the plurality of attachment end openings and the plurality of cleaning end openings are adapted for receiving disposable foam platforms to be dispensed, wherein
  - each disposable foam platform has an attachment end and a cleaning end,
  - the attachment end of each disposable foam platform includes at least one cavity, and
  - the cleaning end is adapted to clean a plurality of female threads of a threaded connector port and an exterior surface of a bore channel within the threaded connector port; and
- a cleaning apparatus for use in connection with the threaded connector port for a feeding tube, the apparatus comprising:
  - a handle body having a longitudinal axis extending from a first end of the handle body to a second end of the handle body, wherein the handle body includes a grip portion extending upwards from the first end of the handle body and a pair of cleaning arms extending downwards from the second end of the handle body,
  - wherein the cleaning apparatus and the foam platform dispenser are adapted to cooperate in dispensing the disposable foam platform, from the foam platform dispenser to the cleaning apparatus, responsive to the handle body being axially aligned with one of the plurality of attachment end openings, the second end of the handle body being pressed onto the attachment end of the disposable foam platform to engage the at least one cavity of the attachment end with the pair of cleaning arms of the handle body, and the attachment end of the disposable foam platform being coupled to the second end of the handle body.

7. The cleaning system of claim 6, wherein the grip portion of the handle body of the cleaning apparatus comprises a pair of gripping arms,
- wherein the pair of cleaning arms are pivotally connected to the gripping arms by a pivot pin enclosed within the handle body, and
- the pair of cleaning arms are urged apart by applying a pressure at the pair of gripping arms in an inward direction towards the longitudinal axis of the handle body such that the pressure is transferred through the pivot pin to urge the pair of cleaning arms apart.

8. The cleaning system of claim 6, wherein the cleaning apparatus further comprises an alignment peg aligned with the longitudinal axis of the handle body and coupled to the second end of the handle body, the alignment peg having an outside diameter smaller than an internal diameter of a bore channel of the threaded connector port and having a length extending beyond the pair of cleaning arms, wherein
- the alignment peg is adapted to be inserted into the bore channel of the threaded connector port such that the cleaning end of a disposable foam platform cleans the plurality of female threads of the threaded connector port and the exterior surface of the bore channel within the threaded connector port when the handle body is rotated radially about the longitudinal axis of the handle body relative to the threaded connector port.

9. A cleaning system for use in connection with enteral feeding, the system comprising:
- a threaded connector port;
- a foam platform dispenser housing having a front side and a back side, wherein
  - the front side has a plurality of attachment end openings and the back side has a plurality of cleaning end openings,
  - the plurality of attachment end openings are axially aligned with the plurality of cleaning end openings, and
  - the plurality of attachment end openings and the plurality of cleaning end openings are adapted for receiving disposable foam platforms to be dispensed, wherein
  - each disposable foam platform includes a tubular hollow portion,
  - each disposable foam platform has an attachment end and a cleaning end,
  - the attachment end of each disposable foam platform includes a pair of cavities, and the cleaning end is adapted to clean a plurality of female threads of the threaded connector port and an exterior surface of a bore channel within the threaded connector port; and
- a cleaning apparatus for use in connection with the threaded connector port for a feeding tube, the apparatus comprising:
  - a handle body having a longitudinal axis extending from a first end of the handle body to a second end of the handle body, wherein
  - the handle body includes a pair of gripping arms extending upwards from the first end of the handle body and a pair of cleaning arms extending downwards from the second end of the handle body,
  - the pair of cleaning arms are pivotally connected to the gripping arms by a pivot pin enclosed within the handle body, and
  - the pair of cleaning arms are urged apart by applying a pressure at the pair of gripping arms in an inward direction towards the longitudinal axis of the handle body such that the pressure is transferred though the pivot pin to urge the pair of cleaning arms apart,
  - an alignment peg aligned with the longitudinal axis of the handle body and coupled to the second end of the handle body, the alignment peg having an outside diameter smaller than an internal diameter of a bore channel of the threaded connector port and having a length extending beyond the pair of cleaning arms, wherein
  - the alignment peg is adapted to be inserted into the bore channel of the threaded connector port such that the cleaning end of a disposable foam platform cleans the plurality of female threads of the threaded connector port and the exterior surface of the bore channel within the threaded connector port when the handle body is rotated radially about the longitudinal axis of the handle body relative to the threaded connector port,
  - the cleaning apparatus and the foam platform dispenser are adapted to cooperate in dispensing the disposable foam platform, from the foam platform dispenser to the cleaning apparatus, responsive to the handle body being axially aligned with one of the plurality of attachment end openings, the second end of the handle body being pressed onto the attachment end of the disposable foam platform to engage the pair of cavities of the attachment end with the pair of cleaning arms of the handle body, and the attachment end of the disposable foam platform being coupled to the second end of the handle body.

10. A cleaning apparatus for use in connection with a threaded connector port for a feeding tube, the apparatus comprising:
- a handle body having a longitudinal axis extending from a first end of the handle body to a second end of the handle body, wherein
- the first end of the handle body includes a grip portion and the second end of the handle body includes at least two cleaning arms,
- the at least two cleaning arms each have a proximal end and a terminal end distally located from the handle body,
- at least one foam pad, wherein the at least one foam pad is coupled to at least one of the at least two cleaning arms,
- the at least one foam pad is adapted to clean female threads of the threaded connector port as the cleaning arms maintain an outward pressure on the at least one foam pad while the handle body is inserted into the threaded connector port and rotated radially about the longitudinal axis of the handle body, and
- the handle body includes a pair of cleats adapted to engage a top surface of a threaded connector port cap when unscrewing the threaded connector port cap.

11. The cleaning apparatus of claim 10, wherein each of the terminal ends of the at least two cleaning arms have an outward facing flange having a height and a width adapted to engage a respective internal female thread of the threaded connector port, the at least two cleaning arms each including a first outer surface, a second outer surface, and a third outer surface along a length of the cleaning arm and outward facing flange,
- the first outer surface extends from the proximal end of the cleaning arms to the terminal end of the cleaning arms,
- the second outer surface extends from the terminal end of the cleaning arms along the width of the outward facing flange, and
- the third outer surface extends from the second outer surface along the height of the outward facing flange.

12. The cleaning apparatus of claim 11, wherein the at least one foam pad comprises a first plurality of foam pads, wherein each foam pad of the first plurality of foam pads is respectively coupled to the first outer surface, the second outer surface, and the third outer surface on each of the at least two cleaning arms.

13. The cleaning apparatus of claim 12, further comprising a second plurality of foam pads, wherein
- each foam pad of the second plurality of foam pads is respectively coupled to a first inner surface and a second inner surface,
- the first inner surface extends from the proximal end of the cleaning arms to the terminal end of the cleaning arms, and
- the second inner surface extends from the terminal end of the cleaning arms along the width of the outward facing flange.

14. The cleaning apparatus of claim 10, wherein the at least two cleaning arms have different lengths.

* * * * *